US009506043B2

(12) United States Patent
Iwai et al.

(10) Patent No.: US 9,506,043 B2
(45) Date of Patent: Nov. 29, 2016

(54) DIAPHORASE

(71) Applicant: TOYOBO CO., LTD., Osaka-shi, Osaka (JP)

(72) Inventors: Sachio Iwai, Tsuruga (JP); Takahide Kishimoto, Tsuruga (JP); Seiji Takeshima, Tsuruga (JP); Shusaku Yanagidani, Tsuruga (JP)

(73) Assignee: TOYOBO CO., LTD., Osaka-shi (JP)

( * ) Notice: Subject to any disclaimer, the term of this patent is extended or adjusted under 35 U.S.C. 154(b) by 82 days.

(21) Appl. No.: 14/367,822

(22) PCT Filed: Dec. 19, 2012

(86) PCT No.: PCT/JP2012/082886
§ 371 (c)(1),
(2) Date: Jun. 20, 2014

(87) PCT Pub. No.: WO2013/094630
PCT Pub. Date: Jun. 27, 2013

(65) Prior Publication Data
US 2015/0344852 A1    Dec. 3, 2015

(30) Foreign Application Priority Data

Dec. 21, 2011  (JP) ................. 2011-279180
Jan. 24, 2012  (JP) ................. 2012-011755
Feb. 15, 2012  (JP) ................. 2012-030161
Oct. 17, 2012  (JP) ................. 2012-229545

(51) Int. Cl.

| | | |
|---|---|---|
| C12N 9/02 | (2006.01) | |
| C12N 1/20 | (2006.01) | |
| C12N 1/00 | (2006.01) | |
| C12N 15/00 | (2006.01) | |
| C12N 5/02 | (2006.01) | |
| C07H 21/04 | (2006.01) | |

(52) U.S. Cl.
CPC ........... *C12N 9/0036* (2013.01); *C12Y 106/99* (2013.01)

(58) Field of Classification Search
None
See application file for complete search history.

(56) References Cited

U.S. PATENT DOCUMENTS

| | | | |
|---|---|---|---|
| 6,146,862 A | 11/2000 | Kawase et al. | |
| 2005/0049313 A1 | 3/2005 | Nishizawa et al. | |
| 2006/0105418 A1 | 5/2006 | Sato et al. | |
| 2007/0196899 A1 | 8/2007 | Goto et al. | |
| 2009/0042232 A1 | 2/2009 | Tokita et al. | |
| 2009/0155880 A1 | 6/2009 | Goto et al. | |
| 2009/0159438 A1 | 6/2009 | Sato et al. | |
| 2009/0166193 A1 | 7/2009 | Sato et al. | |
| 2009/0166194 A1 | 7/2009 | Sato et al. | |
| 2010/0041088 A1 | 2/2010 | Tokita et al. | |

FOREIGN PATENT DOCUMENTS

| | | |
|---|---|---|
| JP | 60-156381 A | 8/1985 |
| JP | 2007-12281 A | 1/2007 |
| JP | 2007-143493 A | 6/2007 |
| JP | 3953578 B2 | 8/2007 |
| JP | 2008-48703 A | 3/2008 |
| JP | 2008-289398 A | 12/2008 |
| JP | 2008-289419 A | 12/2008 |
| JP | 2009-140760 A | 6/2009 |
| JP | 4769412 B2 | 9/2011 |
| JP | 4839569 B2 | 12/2011 |
| WO | 2011/148938 A1 | 12/2011 |

OTHER PUBLICATIONS

Tokita et al., "Sony's Biofuel Cell", ECS Transactions, 13, 21, 2008, pp. 89-97.
Sugiyama et al., "A mediator-adapted diaphorase variant for a glucose dehydrogenase-diaphorase biocatalytic system", Biosensors and Bioelectronics, 26, 2010, pp. 452-457; cited in the Specification.
International Search Report dated Jan. 22, 2013 issued in corresponding application No. PCT/JP2012/082886.
Lucas et al., Database DDBJ/EMBL/GenBank [online], Accession No. CP002293 REGION: 1711200..1711835, <http://www.ncbi.nlm.nih.gov/nuccore/311214252?from=1711200&to=1711835> Nov. 21, 2011 uploaded, [retrieved on Jan. 11, 2013], Definition: *Geobacillus* sp. Y4.1MC1, complete genome; cited in the ISR.
Kaplan et al., "Purification and Properties of a DPNH-TPNH Diaphorase form Clostridium kluyverii", Archives of Biochemistry and Biophysics, 132, 1969, pp. 91-98.
Nazina et al., "Taxonomic study of aerobic thermophilic bacilli: descriptions of Geobacillus subterraneus gen. nov., sp. nov. and *Geobacillus uzenensis* sp. nov. from petroleum reservoirs and trasfer of Bacillus stearothermophilus, Bacillus thermocatenulatus, Bacillus themoleovorans, Bacillus kaustophilus, Bacillus thermoglucosidasius and Bacillus thermodenitrificans to Geobacillus as the new combinations G. stearothermophilus, G. thermocatenulatus, G. thermoleovorans, G. kaustophilus, G. thermoglucosidasius and G. thermodenitrificans", International Journal of Systemic and Evolutionary Microbiology (2001), 51, 433-446.

*Primary Examiner* — Iqbal H Chowdhury
(74) *Attorney, Agent, or Firm* — Westerman, Hattori, Daniels & Adrian, LLP

(57) ABSTRACT

A novel diaphorase; a method for producing the diaphorase; and use of the diaphorase are provided. The diaphorase comprises any one of the following polypeptides (a) to (c): (a) a polypeptide having the amino acid sequence of SEQ ID NO: 1, (b) a polypeptide having the amino acid sequence of SEQ ID NO: 1 in which one or several amino acid residues are substituted, deleted, inserted, added, and/or inverted, and having diaphorase activity, and (c) a polypeptide having an amino acid sequence with 80% or more identity to the amino acid sequence of SEQ ID NO: 1, and having diaphorase activity.

16 Claims, 12 Drawing Sheets

Fig. 1

| | | |
|---|---|---|
| (SEQ ID NO: 3) | AAD24436 | MTNVLYITANPHDDTQSYSMAVGKAFIDTYKQVHPDHEVIHLDLYKEYIPEIDVDVFSGW 60 |
| (SEQ ID NO: 1) | YP_003989131 | MAKLLYITANPKREEESYSLSVGRAFLNAYKQQNPQDEIIELDLYRTDIPYIDADVLNGW 60 |
| | | *::*****:*: : :*::::* :*:,*:*,**:  ,:,** |

| | | |
|---|---|---|
| (SEQ ID NO: 3) | AAD24436 | GKLRSGKSFEELSDEEKAKVGRMNELCEGFISADKYVFVTPMWNFSFPPVLKAYIDAVAV 120 |
| (SEQ ID NO: 1) | YP_003989131 | GKLQQGQSFDGLSAEEKQKISRINELTDGFISADKYVFVTPMWNFSFPPKMKAYIDTICI 120 |
| | | ***:.*::. *** *:.*:* :*************:***::.: |

| | | |
|---|---|---|
| (SEQ ID NO: 3) | AAD24436 | AGKTFKYTEGGPVGLLTDKKALHIQARGGFYSEGPAAEMEMGHRYLSVIMGFFGVPSFEG 180 |
| (SEQ ID NO: 1) | YP_003989131 | AGKTFRYTENGSVGLLTGRKAVHIQARGGIYSEGPTKEVEFGDRYLRAVLGFIGITDVQS 180 |
| | | ***:*:*.****.::**** :*****::*:*:*.*** ::*:*:...: |

| | | |
|---|---|---|
| (SEQ ID NO: 3) | AAD24436 | LFVEGNAAVPEKAEEIKANAIARAKDLAHTF 211 |
| (SEQ ID NO: 1) | YP_003989131 | VIVEGMAQFPNEAESIKENAIKRAEGVAKNF 211 |
| | | ::*** * .*:*:, * ::*:,* |

Fig. 2

| | | |
|---|---|---|
| (SEQ ID NO: 3) | AAD24436 | MTNVLYITANPHDDTQSYSMAVGKAFIDTYKQVHPDHEVIHLDLYKEYIPEIDVDVFSGW 60 |
| (SEQ ID NO: 4) | Variant | MAKLLYITANPKREEESYSLSVGRAFLNAYKQQNPQDEIIELDLYRTDIPYIDADVLNGW 60 |
| | | *::*****:*: : :*::::* :*:,*:*,**:  ,:,** |

| | | |
|---|---|---|
| (SEQ ID NO: 3) | AAD24436 | GKLRSGKSFEELSDEEKAKVGRMNELCEGFISADKYVFVTPMWNFSFPPVLKAYIDAVAV 120 |
| (SEQ ID NO: 4) | Variant | GKLQQGQSFDGLSAEEKQKISRINELTDGFISADKYVFVTPMWNFSFPPKMKAYIDTICI 120 |
| | | ***:.*::. *** *:.*:* :*************:***::.: |

| | | |
|---|---|---|
| (SEQ ID NO: 3) | AAD24436 | AGKTFKYTEGGPVGLLTDKKALHIQARGGFYSEGPAAEMEMGHRYLSVIMGFFGVPSFEG 180 |
| (SEQ ID NO: 4) | Variant | ADKTFRYTENGSVGLLTGRKAVHIQARGGIYSEGPTKEVEFGDRYLRAVLGFIGITDVQS 180 |
| | | *.*:*:*.****.::**** :*****::*:*:*.*** ::*:*:...: |

| | | |
|---|---|---|
| (SEQ ID NO: 3) | AAD24436 | LFVEGNAAVPEKAEEIKANAIARAKDLAHTF 211 |
| (SEQ ID NO: 4) | Variant | VIVEGMAQFPNEAESIKENAIKRAEGVAKNF 211 |
| | | ::*** * .*:*:, * ::*:,* |

Fig. 3
(A) SDS-PAGE
(B) Gel filtration
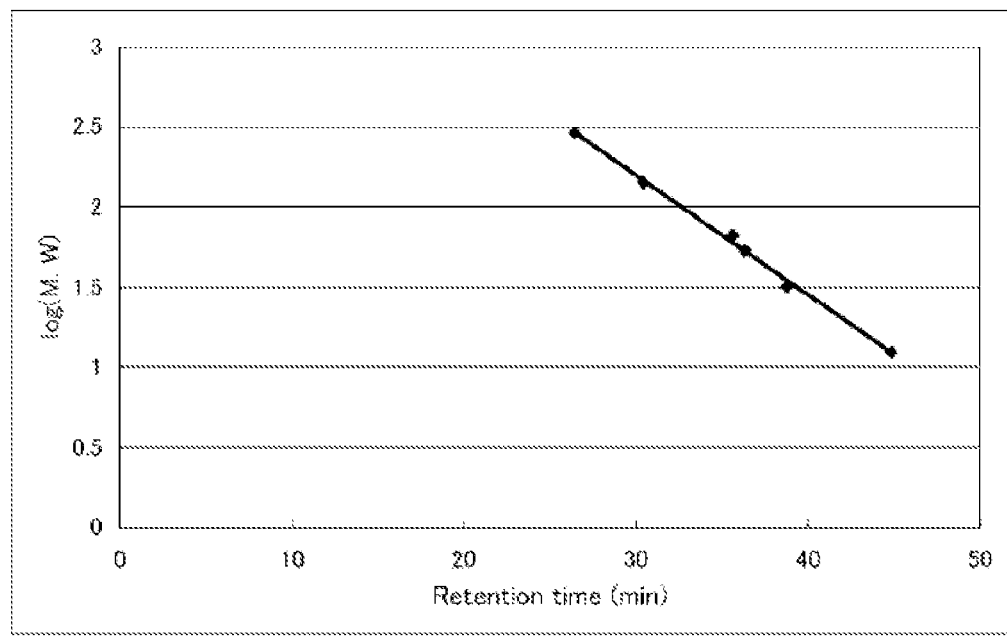

Fig. 4
(A) SDS-PAGE
(B) Gel filtration
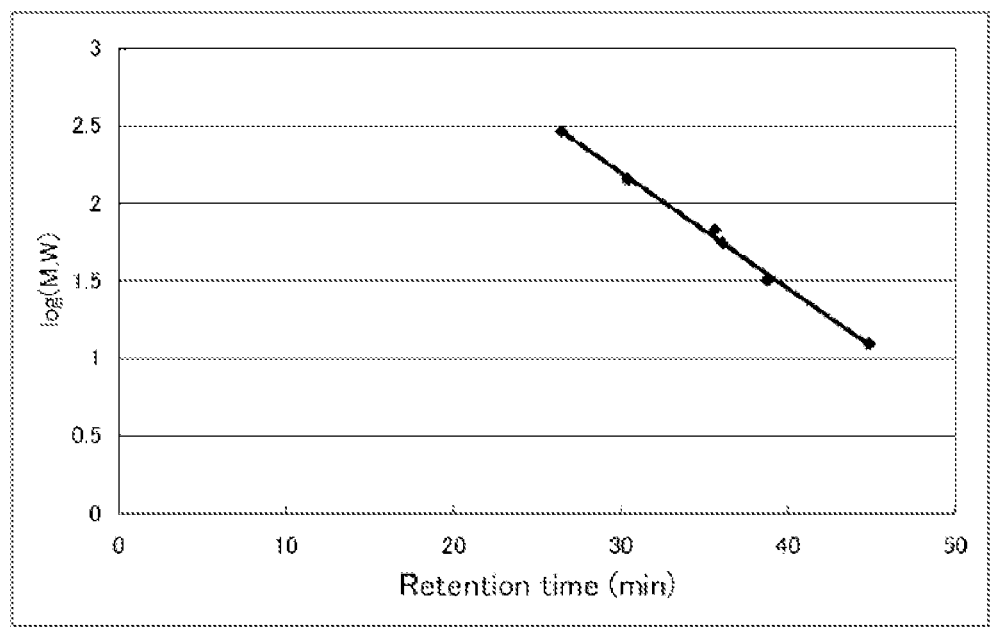

Fig. 5
(A) *Geobacillus* sp. Y4.1MC1-derived wild-type
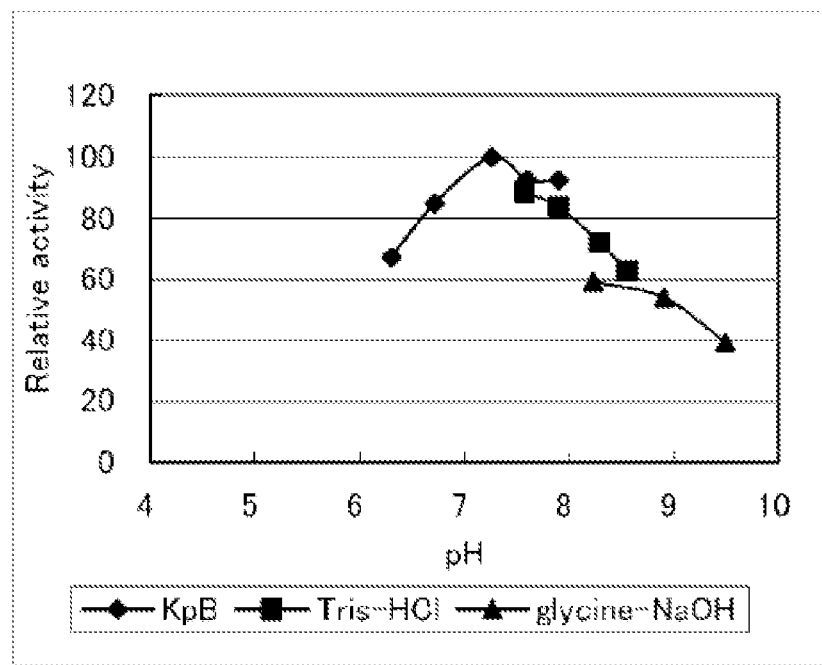
(B) *Geobacillus* sp. Y4.1MC1-derived variant
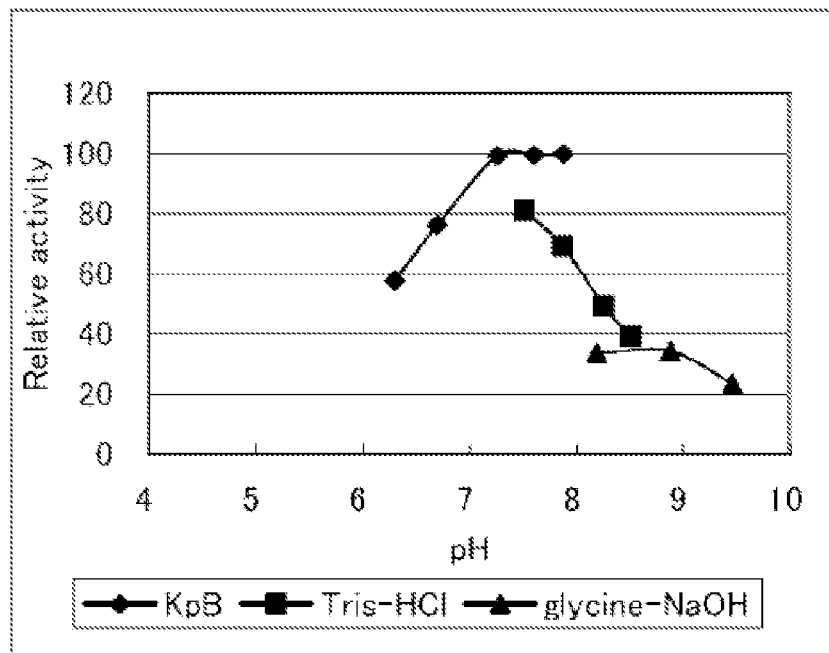

Fig. 6
(A) *Geobacillus* sp. Y4.1MC1-derived wild-type
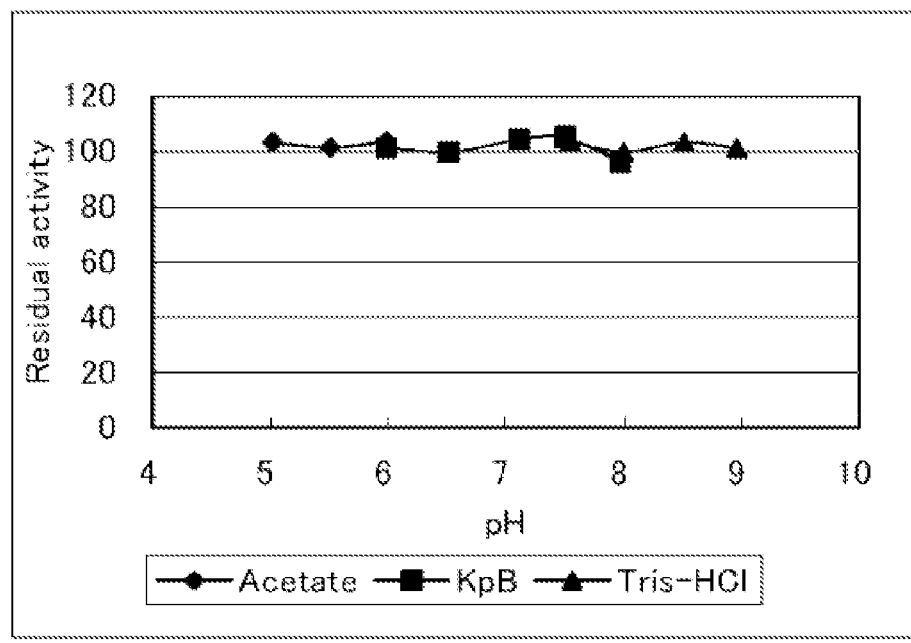
(B) *Geobacillus* sp. Y4.1MC1-derived variant
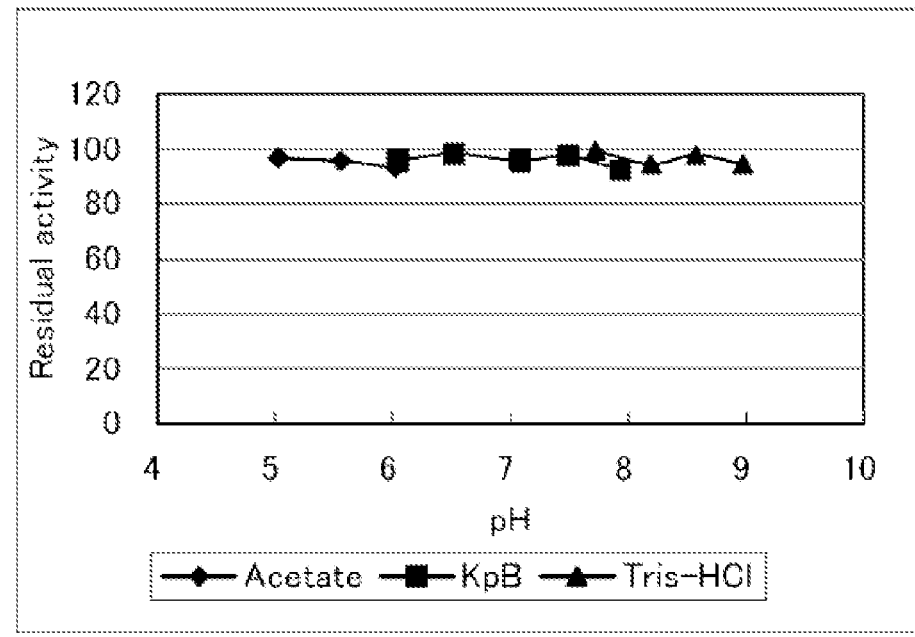

Fig. 7
(A) *Geobacillus* sp. Y4.1MC1-derived wild-type
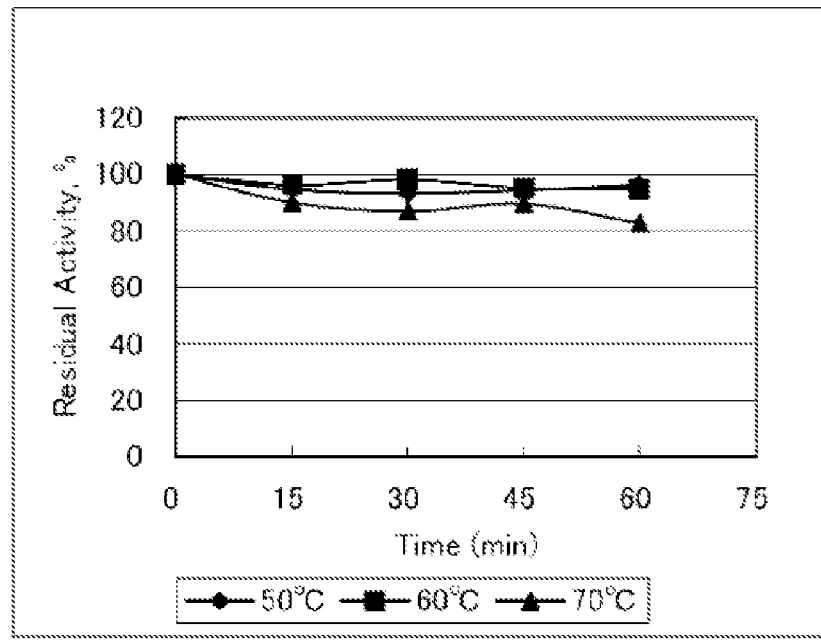
(B) *Geobacillus* sp. Y4.1MC1-derived variant
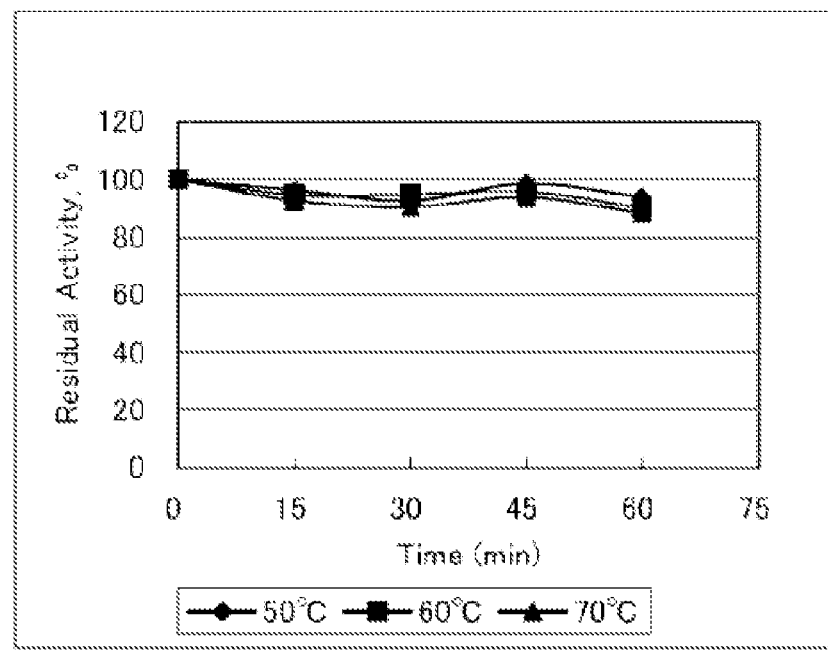

Geobacillus stearothermophilus-derived diaphorase

Fig. 9
(A) *Geobacillus* sp. Y4.1MC1-derived wild-type
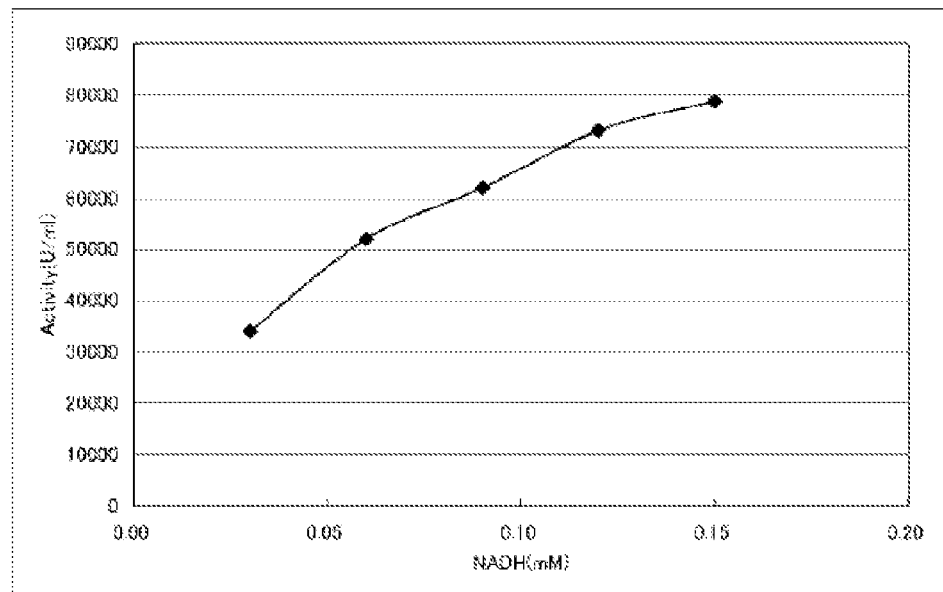
(B) *Geobacillus* sp. Y4.1MC1-derived variant
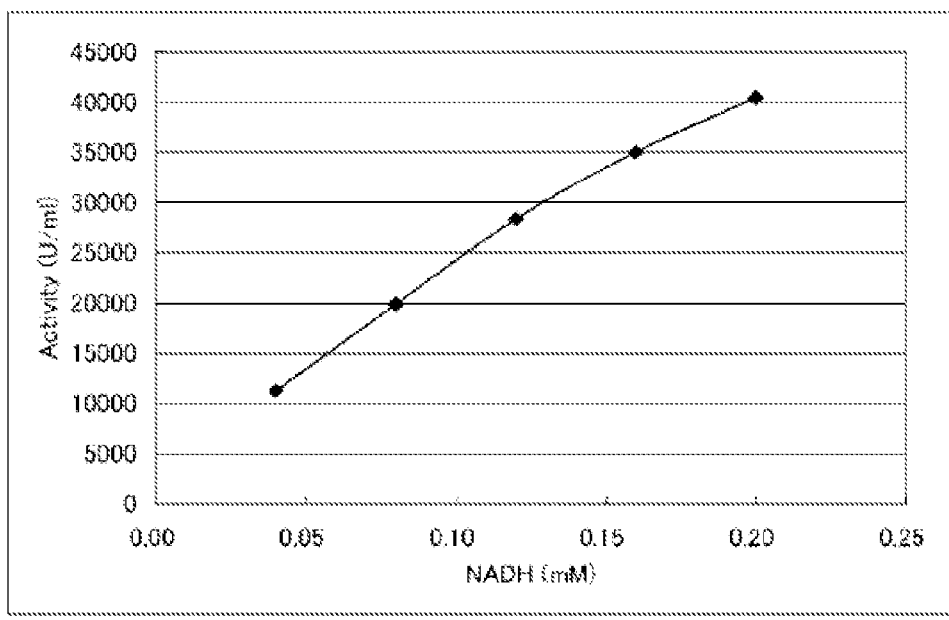

Geobacillus stearothermophilus-derived diaphorase

Fig. 11
(A)
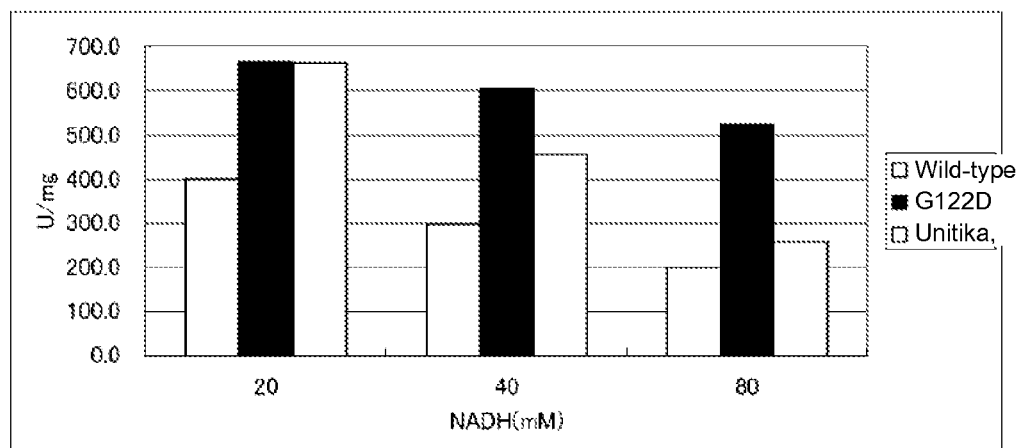
(B)
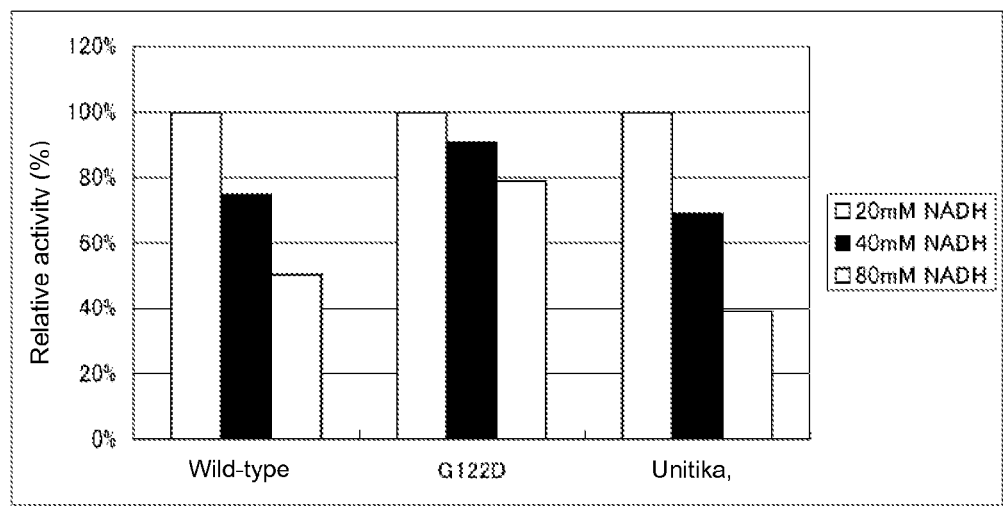

Fig. 12
(A) Relationship between the reaction temperature and the relative activity, when DCPIP is used as a mediator
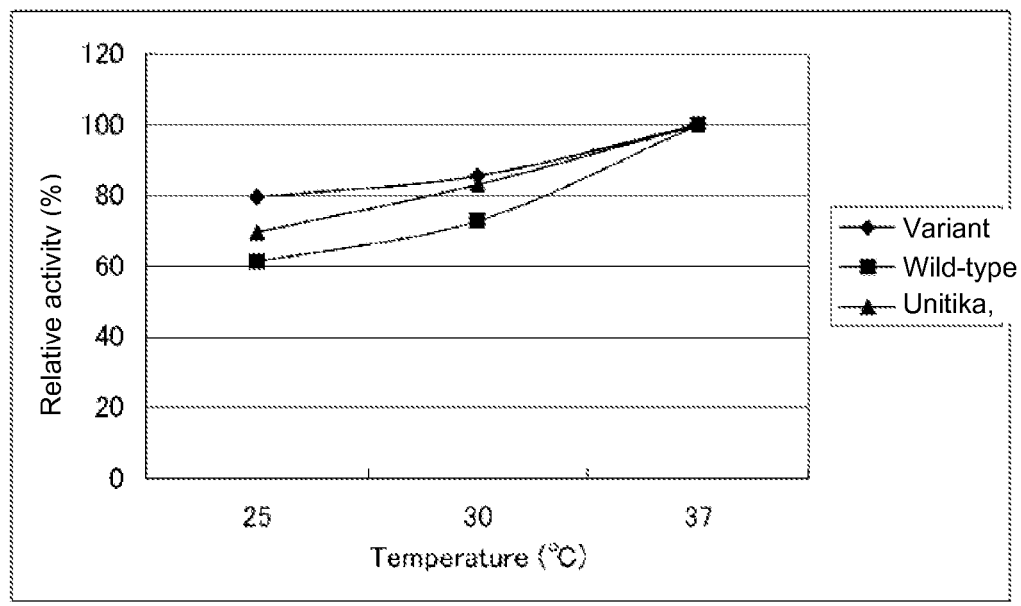
(B) Relationship between the reaction temperature and the specific activity, when DCPIP is used as a mediator
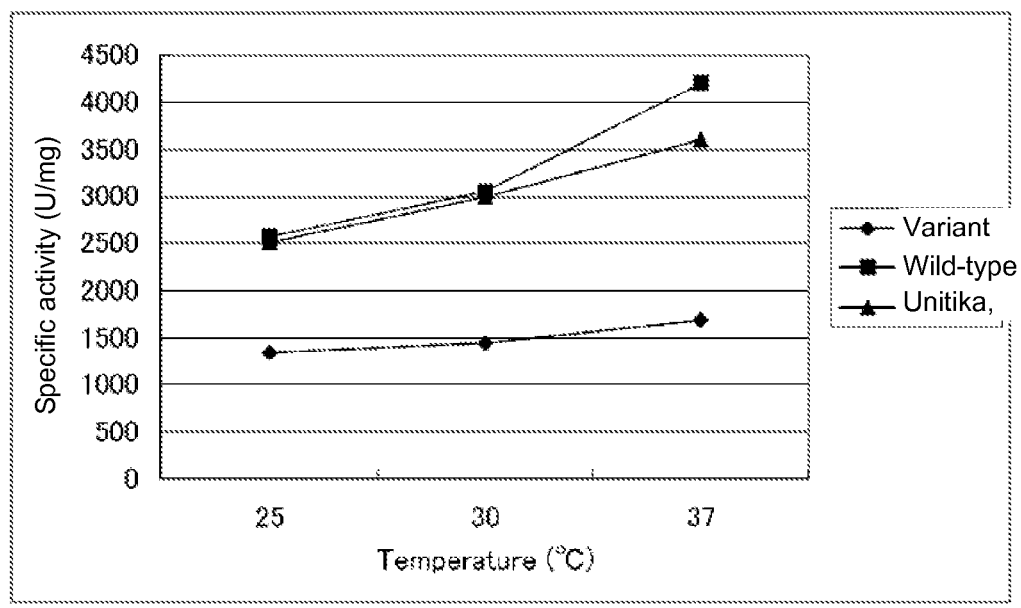

Fig. 13
(A) Relationship between the reaction temperature and the relative activity, when ANQ is used as a mediator
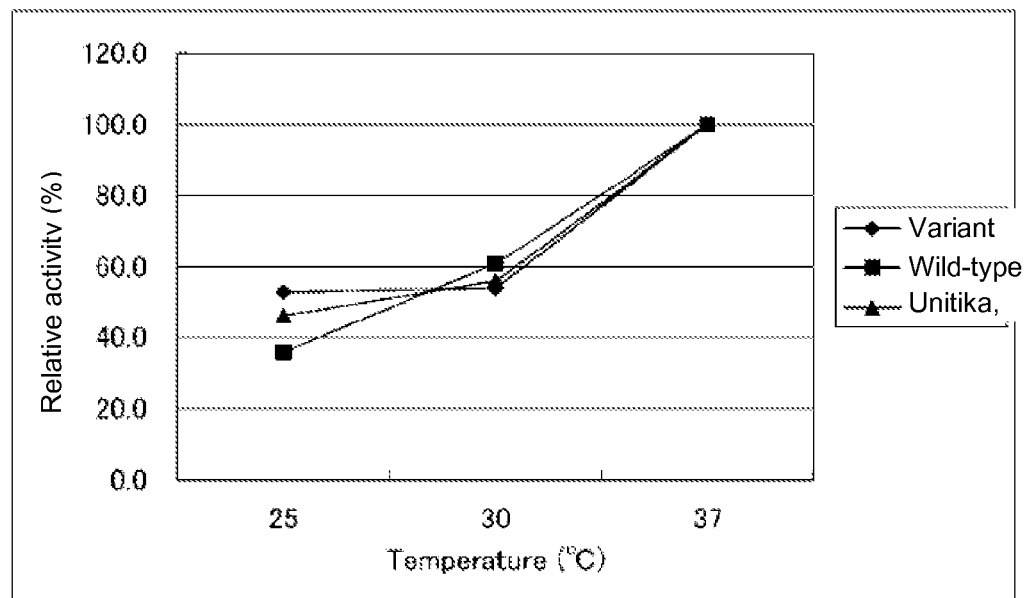
(B) Relationship between the reaction temperature and the specific activity, when ANQ is used as a mediator
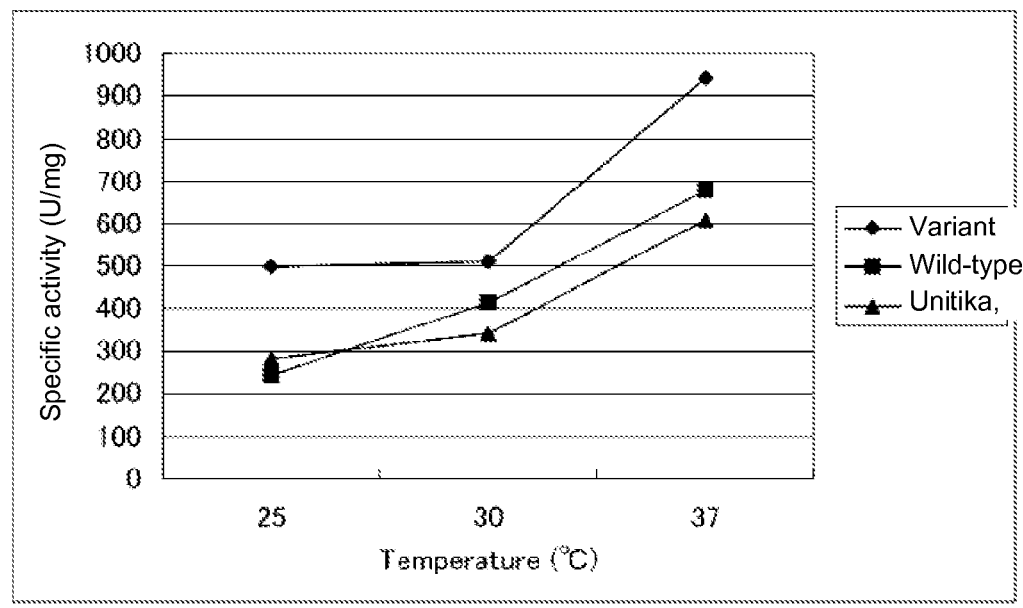

DIAPHORASE

TECHNICAL FIELD

The present invention relates to a diaphorase. Specifically, the invention relates to an enzyme having diaphorase activity, DNA encoding it, a fungus that produces the enzyme, a method for producing the enzyme; and a clinical-diagnostic agent, enzyme electrode, enzyme sensor, and the like using the enzyme.

BACKGROUND ART

Diaphorases (EC.1.6.99.-) play an important role in electron transport systems in vivo.

In various technical fields, the use of diaphorases in vitro has been studied and some of them have been put to practical use. Examples of such technical fields include the production of useful material, the production, measurement or analysis of energy-related material, environmental protection, medical, and other fields. For example, in the field of clinical diagnosis, utilizing the property of diaphorases that it uses reduced nicotinamide adenine dinucleotide (NADH) or reduced nicotinamide adenine dinucleotide phosphate phosphate (NADPH) as a substrate, diaphorases are used to form various in vitro diagnostic reagents. A diaphorase is also used as an enzyme cell, which is one type of fuel cell (Patent Document 9, Patent Document 10, Patent Document 11, Non-patent Document 1).

Commercially available diaphorases include those isolated and purified from microorganisms that belong to the genus *Clostridium* (Non-patent Document 2) or *Bacillus* (Patent Document 1, Patent Document 2). *Bacillus stearothermophilus* that is capable of producing the diaphorase described in Patent Document 1 and Patent Document 2 was reclassified as *Geobacillus stearothermophilus* in 2001 (Non-patent Document 3). Diaphorase derived from *Geobacillus stearothermophilus* and modifications thereof are also known, and their gene sequences, amino acid sequences, and physicochemical characteristics are being studied (Patent Document 2, Patent Document 3, Patent Document 8, and Non-patent Document 1).

CITATION LIST

Patent Documents

Patent Document 1: JPS60-156381A
Patent Document 2: JP3953578B
Patent Document 3: JP2007-143493A
Patent Document 4: JP2008-048703A
Patent Document 5: JP2008-289398A
Patent Document 6: JP2008-289419A
Patent Document 7: JP4769412B
Patent Document 8: WO2011/148938
Patent Document 9: JP2009-140760A
Patent Document 10: JP4839569B
Patent Document 11: JP2007-12281A

Non-Patent Documents

Non-patent Document 1: Sugiyama et al., Biosens Bioelectron. 2010 Oct. 15; 26(2): 452-7. Epub 2010 Aug. 3.
Non-patent Document 2: Kaplan, N. O., et al., Arch. Biochem. Biophys, Vol. 132, P. 91-98, 1969
Non-patent Document 3: T. N. Nazina, Int. Jour. Syst. Evol. Micro. 51: 433-446. 2001
Non-patent Document 4: Tokita et al., ECS Transactions. 2008; 13(21): 89-97.

SUMMARY OF INVENTION

Technical Problem

The present invention provides a novel diaphorase that is more suitable for use in clinical diagnosis and industrial applications.

Solution to Problem

The present inventors conducted intensive research to achieve the above use. As a result of screening many microorganisms and genetic information that had not been reported to produce a diaphorase, and to encode a protein having diaphorase activity, the present inventors found that novel gene sequences derived from a microorganism belonging to the genus *Geobacillus* sp. Y4.1MC1 encode a protein having diaphorase activity. The present inventors isolated and purified the enzyme, analyzed its properties, and thereby found that the enzyme has excellent heat resistance, and high affinity for NADH. The present inventors then conducted further research and accomplished an invention related to a diaphorase and relevant thereto, and filed Japanese Patent Application No. 2012-011755.

Based on these findings, the present inventors conducted further research to provide a novel diaphorase that is more suitable for use in clinical diagnosis and industrial application by applying modifications through a protein engineering technique.

In this process, the present inventors found that if the reaction of diaphorase is conducted under conditions of a high concentration of substrate such as NADH, the enzymatic reaction is inhibited. According to enzyme kinetics, it is believed that, generally, when the substrate concentration is higher than the Km value, the enzyme can easily form a complex with the substrate, allowing the catalytic reaction to proceed efficiently. However, the findings were surprisingly contrary to this.

Due to such properties, for example, in fuel cells, the addition amount of NADH (i.e., the substrate) cannot be increased, making it difficult to obtain satisfactory electromotive force or product life.

Under the above circumstances, in order to solve the newly found problem, the present inventors applied modifications to the diaphorase through a protein engineering technique, and found that a variant diaphorase has the properties described above and exhibits reduced reaction inhibition even at a high concentration of substrate such as NADH. The present invention has been accomplished based on these findings. Representative examples of the invention are described below.

Item 1.

A diaphorase comprising any one of the following polypeptides (a) to (c):

(a) a polypeptide having the amino acid sequence of SEQ ID NO: 1, (b) a polypeptide having the amino acid sequence of SEQ ID NO: 1 in which one or several amino acid residues are substituted, deleted, inserted, added, and/or inverted, and having diaphorase activity, and (c) a polypeptide having an amino acid sequence with 80% or more identity to the amino acid sequence of SEQ ID NO: 1, and having diaphorase activity.

Item 2.

A diaphorase having the following properties (1) to (5):

(1) Subunit molecular weight: the molecular weight of a polypeptide moiety in the enzyme is about 23.7 kDa as measured by SDS-polyacrylamide electrophoresis, (2) Composite molecular weight: the molecular weight of a polypeptide moiety in the enzyme is about 53.3 kDa as measured by gel filtration, (3) Km value: the Km value for NADH is about 0.1 mM or less, (4) Temperature stability: stable at a temperature of 70° C. or lower, and (5) pH stability: stable at a pH range of 5.0 to 9.0.

Item 3.

The diaphorase according to Item 1 or Item 2, which is a variant diaphorase having any one of the following polypeptides (a) to (c):

(a) a polypeptide having the amino acid sequence of SEQ ID NO: 4, (b) a polypeptide having the amino acid sequence of SEQ ID NO: 4 in which one or several amino acid residues are substituted, deleted, inserted, added, and/or inverted at a site other than position 122, and having diaphorase activity, and (c) a polypeptide having an amino acid sequence with 80% or more identity to the amino acid sequence of SEQ ID NO: 4, the glycine at position 122 being modified to aspartic acid in the alignment of the SEQ ID NO: 4, and having diaphorase activity.

Item 4.

The variant diaphorase according to Item 3, which further has one or more of the following properties (d) and (e):

(d) when the specific activity in the presence of 20 mM NADH is taken as 100%, the specific activity in the presence of 80 mM NADH can be maintained at 50% or more, and (e) (1) when DCPIP is used as a mediator and the activity value at 37° C. is taken as 100%, the relative activity at 25° C. is 70% or more, or (2) when a naphthoquinone derivative is used as a mediator and the activity value at 37° C. is taken as 100%, the relative activity at 25° C. is 50% or more.

Item 5.

The variant diaphorase according to Item 3 or 4, which further has the following property (f):

(f) when a naphthoquinone derivative is used as a mediator, the specific activity is at least 1.5 times that of a wild-type diaphorase.

Item 6.

A DNA of any one of the following (A) to (F):

(A) DNA encoding the amino acid sequence of SEQ ID NO: 1, (B) DNA having the base sequence of SEQ ID NO: 2, (C) DNA having a base sequence with 80% or more homology to the base sequence of SEQ ID NO: 2, and encoding a polypeptide having diaphorase activity, (D) DNA hybridizing to a base sequence complementary to the base sequence of SEQ ID NO: 2 under stringent conditions, and encoding a polypeptide having diaphorase activity, (E) DNA having the base sequence of SEQ ID NO: 2 in which one or several bases are substituted, deleted, inserted, added, and/or inverted, and encoding a polypeptide having diaphorase activity, and (F) DNA having the amino acid sequence of SEQ ID NO: 1 in which one or several amino acid residues are substituted, deleted, inserted, added, or inverted, and encoding a polypeptide having diaphorase activity.

Item 7.

The DNA according to Item 6, which is any one of the following (A) to (F):

(A) DNA encoding the amino acid sequence of SEQ ID NO: 4, (B) DNA having the base sequence of SEQ ID NO: 5, (C) DNA having a base sequence with 80% or more identity to the base sequence of SEQ ID NO: 5, in the alignment of SEQ ID NO: 5, a triplet at positions 364 to 366 encoding an aspartic acid, and encoding a polypeptide having diaphorase activity, (D) DNA hybridizing to a base sequence complementary to the base sequence of SEQ ID NO: 5 under stringent conditions, wherein a triplet at positions 364 to 366 in the alignment of SEQ ID NO: 5 encodes an aspartic acid, and wherein the DNA encodes a polypeptide having diaphorase activity, (E) DNA having the base sequence of SEQ ID NO: 5, in which one or several bases are substituted, deleted, inserted, added, and/or inverted, wherein a triplet at positions 364 to 366 in the alignment of SEQ ID NO: 5 encodes an aspartic acid, and wherein the DNA encodes a polypeptide having diaphorase activity, and (F) DNA encoding a polypeptide having the amino acid sequence of SEQ ID NO: 4, in which one or several amino acid residues are substituted, deleted, inserted, added, or inverted at a position other than position 122, and having diaphorase activity.

Item 8.

A vector containing the DNA of Item 6 or 7.

Item 9.

A transformant containing the vector of Item 8.

Item 10.

A method for producing the diaphorase of any one of Items 1 to 5, the method comprising culturing the transformant of Item 9.

Item 11.

A product comprising the diaphorase of any one of Items 1 to 5.

Item A.

The diaphorase according to Item 2, which further has the following property (6):

(6) Optimal activity pH: 6.7 to 8.0

Item B.

The diaphorase according to Item 2 or Item A, which further has the following property (7):

(7) Origin: the enzyme is derived from microorganisms of the genus *Geobacillus*.

Item C.

A method for producing the diaphorase of any one of Items 2, A and B, the method comprising:

culturing microorganisms of the genus *Geobacillus* and collecting diaphorase.

Item D.

A variant diaphorase having the following properties (1) to (4):

(1) Subunit molecular weight: the molecular weight of a polypeptide moiety in the enzyme is about 23.7 kDa as measured by SDS-polyacrylamide electrophoresis, (2) Composite molecular weight: the molecular weight of a polypeptide moiety in the enzyme is about 55.3 kDa as measured by gel filtration, and (3) Km value: the Km value for NADH is about 0.37 mM or less.

Item E.

The variant diaphorase according to Item D, further having the following properties (4) and/or (5):

(4) Temperature stability: stable at a temperature of 70° C. or lower, and
(5) pH stability: stable at a pH range of 5.0 to 9.0.
Item F.
The variant diaphorase according to Item D or Item E, further having the following property (6):
(6) Optimal activity pH: 6.5 to 8.0 Item G.
The variant diaphorase according to any one of Item D to Item F, further having the following property (7): (7) Origin: the enzyme is derived from microorganisms of the genus *Geobacillus*
Item H.
The method for producing a variant diaphorase according to any one of Item D to Item G, which further comprises culturing microorganisms of the genus *Geobacillus* and collecting diaphorase.

Advantageous Effects of Invention

The diaphorase of the present invention has diaphorase activity, and a high affinity for NADH (i.e., has a significantly small Km value for NADH), and thus enables reaction with NADH in a sample in a shorter period of time with a smaller amount of enzyme. Furthermore, the diaphorase of the present invention exhibits excellent thermal stability, allowing fixation to a sensor strip under relatively high temperature conditions. The diaphorase of the present invention is also stable in a wide range of pH; therefore, it is suitably used under various conditions. Having the above properties, the diaphorase of the invention can accurately measure glucose concentration in any sample containing NADH (e.g., blood and food (such as seasonings and beverages)). Further, the DNA of the invention encodes the diaphorase of the invention, and the diaphorase of the invention can thus be efficiently produced by using genetic engineering techniques.

Because the diaphorase of the present invention allows the reaction to effectively proceed even when the concentration substrate such as NADH is high, a long product life and satisfactory electromotive force can be obtained when the diaphorase is used for a fuel cell.

BRIEF DESCRIPTION OF DRAWINGS

FIG. 1 shows alignments of a diaphorase (ACCESSION AAD24436) of *Geobacillus stearothermophilus* and NAD(P)H dehydrogenase (ACCESSION YP_003989131) of *Geobacillus* sp. Y4.1MC1

FIG. 2 shows the identification of a polypeptide sequence of *Geobacillus* sp. Y4.1MC1-derived variant diaphorase. (D) Alignments of diaphorase (ACCESSION AAD24436) of *Geobacillus stearothermophilus* and variant diaphorase of *Geobacillus* sp. Y4.1MC1.

FIG. 3(A) shows the SDS-PAGE results of the purified enzyme *Geobacillus* sp. Y4.1MC1-derived wild-type diaphorase; FIG. 3(B) shows the results of gel filtration of a purified enzyme of *Geobacillus* sp. Y4.1MC1-derived wild-type diaphorase.

FIG. 4(A) shows the SDS-PAGE results of a purified enzyme of *Geobacillus* sp. Y4.1MC1-derived variant diaphorase. FIG. 4(B) shows the gel filtration results of a purified enzyme of *Geobacillus* sp. Y4.1MC1-derived variant diaphorase.

FIG. 5(A) shows the influence of pH on the activity of *Geobacillus* sp. Y4.1MC1-derived wild-type diaphorase. FIG. 5(B) shows the influence of pH on the activity of *Geobacillus* sp. Y4.1MC1-derived variant diaphorase.

FIG. 6(A) shows the measurement results of pH stability of *Geobacillus* sp. Y4.1MC1-derived wild-type diaphorase. FIG. 6(B) shows the measurement results of pH stability of *Geobacillus* sp. Y4.1MC1-derived variant diaphorase.

FIG. 7(A) shows the measurement results of temperature stability of *Geobacillus* sp. Y4.1MC1-derived wild-type diaphorase. FIG. 7(B) shows the the measurement results of temperature stability of *Geobacillus* sp. Y4.1MC1-derived variant diaphorase.

FIG. 9(A) shows the relationship between the reaction rate of *Geobacillus* sp. Y4.1MC1-derived wild-type diaphorase and the NADH concentration. FIG. 9(B) shows the relationship between the reaction rate of *Geobacillus* sp. Y4.1MC1-derived variant diaphorase and the NADH concentration.

FIG. 11(A) shows the relationship between the NADH concentration and the specific activity, when ANQ is used as a mediator, in terms of *Geobacillus* sp. Y4.1MC1-derived wild-type diaphorase, *Geobacillus* sp. Y4.1MC1-derived variant diaphorase, and *Geobacillus stearothermophilus*-derived diaphorase (produced by Unitika Ltd.). FIG. 11(B) shows the relationship between the NADH concentration and the reduction of the specific activity, when ANQ is used as a mediator, in terms of *Geobacillus* sp. Y4.1MC1-derived wild-type diaphorase, *Geobacillus* sp. Y4.1MC1-derived variant diaphorase, and *Geobacillus stearothermophilus*-derived diaphorase (produced by Unitika Ltd.).

FIG. 12(A) shows the relationship between the reaction temperature and the relative activity, when DCPIP is used as a mediator, in terms of *Geobacillus* sp. Y4.1MC1-derived wild-type diaphorase, *Geobacillus* sp. Y4.1MC1-derived variant diaphorase, and *Geobacillus stearothermophilus*-derived diaphorase (produced by Unitika Ltd.). FIG. 12(B) shows the relationship between the reaction temperature and the specific activity, when DCPIP is used as a mediator, in terms of *Geobacillus* sp. Y4.1MC1-derived wild-type diaphorase, *Geobacillus* sp. Y4.1MC1-derived variant diaphorase, and *Geobacillus stearothermophilus*-derived diaphorase (produced by Unitika Ltd.).

FIG. 13(A) shows the relationship between the reaction temperature and the relative activity, when ANQ is used as a mediator, in terms of *Geobacillus* sp. Y4.1MC1-derived wild-type diaphorase, *Geobacillus* sp. Y4.1MC1-derived variant diaphorase, and *Geobacillus stearothermophilus*-derived diaphorase (produced by Unitika Ltd.). FIG. 13(B) shows the relationship between the reaction temperature and the relative activity, when ANQ is used as a mediator, in terms of *Geobacillus* sp. Y4.1MC1-derived wild-type diaphorase, *Geobacillus* sp. Y4.1MC1-derived variant diaphorase, and *Geobacillus stearothermophilus*-derived diaphorase (produced by Unitika Ltd.).

DESCRIPTION OF EMBODIMENTS

Figure 8:
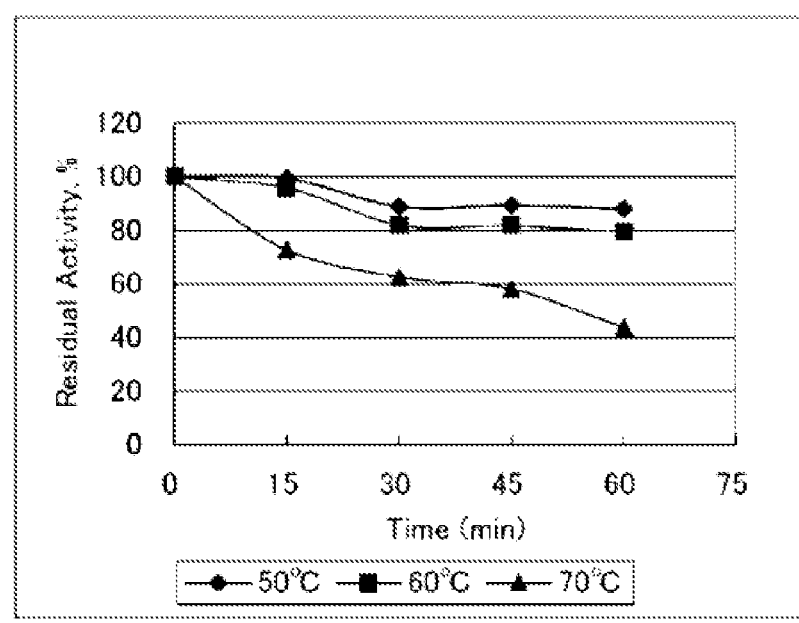
FIG. 8 shows the the measurement results of temperature stability of *Geobacillus stearothermophilus*-derived diaphorase (produced by Unitika Ltd.).

The present invention is described below in detail.
1. Diaphorase
1-1. Diaphorase Activity
A "diaphorase" is an enzyme having an activity (i.e., diaphorase activity) for catalyzing the reaction of oxidizing NADH or NADPH with dyes such as potassium ferricyanide, methylene blue, 2,6-dichloroindophenol (DCPIP), and tetrazolium salt. A diaphorase exhibits a wide distribution to microorganisms, such as bacteria and yeast, and mammals. Diaphorases play an important role in electron transport systems in vivo. Attributable to diaphorase, NAD or NADP generated from a substrate by a dehydrogenation reaction using NADH or NADPH dependent dehydrogenases is oxidized in an electron acceptor, and the electron acceptor becomes a reduced form.

Diaphorase activity can be measured by known methods. For example, the activity can be measured using DCPIP as an electron acceptor and based on the change in the absorbance of a sample at a wavelength of 600 nm before and after reaction. Diaphorase dehydrogenase activity can also be measured by using ANQ as an electron acceptor and based on the change in the absorbance of a sample at a wavelength of 520 nm before and after reaction. More specifically, the activity can be measured using the following reagent and under the following measurement conditions.

1-1-1. Method for Measuring Diaphorase Activity Using DCPIP
Reagent
Distilled water
200 mM Tris-HCl buffer solution pH of 7.5
6.0 mM NADH aqueous solution
1.2 mM 2,6-dichlorophenolindophenol (DCPIP) solution
Enzyme diluting solution: 200 mM Tris-HCl buffer solution containing 0.1% bovine serum albumin at pH of 7.5
Procedure 1
A diaphorase solution is diluted to 0.4 to 0.8 U/mL with the aforementioned enzyme diluting solution that was ice-cooled in advance, followed by storage on ice to prepare an enzyme solution.
Procedure 2
The aforementioned distilled water (2.4 mL), Tris-HCl buffer solution (0.3 mL), and NADH aqueous solution (0.1 mL) are mixed and preliminarily heated at 25° C. for 5 minutes to prepare a reaction mixture.
Measurement Conditions
To the reaction solution (2.8 mL), an enzyme solution (0.1 mL) and a DCPIP solution (0.1 mL) are added in this order and gently mixed. Water is used as a control, and changes in absorbance at 600 nm are recorded for 2 to 3 minutes by a spectrophotometer at a controlled temperature of 25° C. (optical path length: 1.0 cm). Based on the linear portion (i.e., after the reaction rate becomes constant), the change in absorbance per minute ($\Delta OD_{TEST}$) is measured. In a blind test, the enzyme diluting solution used for dissolving diaphorase and a DCPIP solution are added to the reagent mixture in place of the enzyme solution, and the change in absorbance per minute ($\Delta OD_{BLANK}$) is measured in a similar manner. Based on the obtained values, the diaphorase activity is determined by the following equation. Here, one unit (U) of diaphorase activity is equal to the amount of enzyme that reduces absorbance of a sample by 1.0 at a wavelength of 600 nm in 1 minute.

$$\text{Activity(U/mL)} = \{-(\Delta OD_{TEST} - \Delta OD_{BLANK}) \times \text{dilution rate}\}/(1.0 \times 0.1)$$

In the equation, 1.0 indicates a unit absorbance at a wavelength of 600 nm based on the activity definition, and 0.1 indicates the liquid amount (mL) of enzyme solution. In this specification, when DCPIP is used as a mediator, the enzyme activity is measured according to the above measurement method. In Examples 6 to 14 described later, the diaphorase activity is measured according to the above measurement method.

1-1-2. Method for Measuring Diaphorase Activity Using ANQ
Reagent
Distilled water
100 mM potassium phosphate buffer solution (pH of 8.0)
100 mM 2-amino-1,4-naphthoquinone (ANQ) solution (dissolved in DMSO)
100 mM potassium phosphate buffer solution (pH of 8.0) containing
400 mM NADH
200 mM potassium phosphate buffer solution containing enzyme diluting solution containing 0.1% TritonX-100 (pH of 7.5)
Procedure 1
A diaphorase solution is diluted to 0.01 to 0.02 mg/mL with the aforementioned enzyme solution that was ice-cooled in advance, followed by storage in ice to prepare an enzyme solution.
Procedure 2
The aforementioned 100 mM sodium phosphate buffer solution (79.0 mL), 100 mM 2-amino-1,4-naphthoquinone (which may be referred to as ANQ in this specification) solution (1.0 mL), and 100 mM sodium phosphate buffer solution (20 mL) containing 400 mM NADH are mixed to prepare a 100 mL mixture solution. This procedure allows an NADH mixture solution having a final concentration of 80 mM to be prepared.

In order to prepare a mixture solution having a different NADH concentration, the mixing amount of the 100 mM sodium phosphate buffer solution and the 400 mM NADH-containing 100 mM sodium phosphate buffer solution is changed to adjust the concentration of the mixture solution. For example, a 100 mM sodium phosphate buffer solution (89.0 mL), 100 mM 2-amino-1,4-naphthoquinone (ANQ) solution (1.0 mL), and 400 mM NADH-containing 100 mM sodium phosphate buffer solution (10 mL) are mixed to prepare a 100 mL mixture solution, obtaining a mixture solution having a final NADH concentration of 40 mM. Alternatively, a 100 mM sodium phosphate buffer solution (94.0 mL), 100 mM 2-amino-1,4-naphthoquinone (ANQ) solution (1.0 mL), and 400 mM NADH-containing 100 mM sodium phosphate buffer solution (5 mL) are mixed to prepare a 100 mL mixture solution, obtaining a mixture solution having a final NADH concentration of 20 mM.
Procedure 3
From the mixture solution prepared in Procedure 2, 3.0 mL thereof was extracted and pre-heated at 25° C. for 5 minutes to prepare a reaction mixture.
Measurement Conditions
To the reaction solution (3.0 mL), enzyme solution (0.1 mL) is added and gently mixed. Water is used as a control, and changes in absorbance at 520 nm are recorded for 2 to 3 minutes by a spectrophotometer at a controlled temperature of 25° C. (optical path length: 1.0 cm). Based on the linear portion (i.e., after the reaction rate becomes constant), the change in absorbance per minute ($\Delta OD_{TEST}$) is measured. In a blind test, a enzyme diluting solution used for dissolving diaphorase is added to the reaction mixture in place of the enzyme solution, and the change in absorbance per minute ($\Delta OD_{BLANK}$) is measured in a similar manner. Based on the obtained values, the diaphorase activity is determined by the following equation. Here, one unit (U) of diaphorase activity is equal to the amount of enzyme that reduces absorbance of a sample by 1.0 at a wavelength of 520 nm in 1 minute.

$$\text{Activity(U/mL)} = \{-(\Delta OD_{TEST} - \Delta OD_{BLANK}) \times 3.1 \times \text{dilution rate}\}/\{0.68 \times 0.1 \times 1.0\}$$

In the equation, 3.1 is the total liquid amount (mL) of the reaction reagent and the enzyme solution, 0.68 is the millimolar extinction coefficient (cm$^2$/μmol) under the conditions in which the activity is measured, 0.1 is the liquid amount (mL) of the enzyme solution, and 1.0 is the optical path length (cm) of the cell. In this specification, when ANQ is used as a mediator, the enzyme activity is measured according to the above measurement method, unless otherwise indicated. In Example 15 described later, the diaphorase activity was measured according to the above measurement method.

The diaphorase of the present invention is preferably isolated diaphorase or purified diaphorase. The diaphorase of the present invention may be dissolved in a solution described above that is suitable for the storage method described later or in a freeze-dried state (e.g., powder). The expression "isolated" used in regard to the enzyme (diaphorase) of the present invention refers to a state in which the enzyme is substantially free of components (e.g., host-cell-derived contaminating proteins, other components, and culture media) other than the enzyme. Specifically, for example, the isolated enzyme of the present invention contains contaminating proteins in an amount of less than about 20%, preferably less than about 10%, more preferably less than about 5%, and even more preferably less than about 1%, of the total (by weight). It is also possible for the diaphorase of the present invention to be present in a solution (e.g., buffer) suitable for storage or for measurement of enzyme activity.

1-2. Polypeptide

The diaphorase of the present invention preferably comprises any one of the following polypeptides (a) to (c):

(a) a polypeptide having the amino acid sequence of SEQ ID NO: 1, (b) a polypeptide having the amino acid sequence of SEQ ID NO: 1 in which one or several amino acid residues are substituted, deleted, inserted, added, and/or inverted, and having diaphorase activity, and (c) a polypeptide having an amino acid sequence with 80% or more identity to the amino acid sequence of SEQ ID NO: 1, and having diaphorase activity.

As shown in Example 5, the amino acid sequence of SEQ ID NO: 1 is equal to the amino acid sequence of a diaphorase derived from *Geobacillus* sp. Y4.1MC1 and exhibits all of the properties described in Sections 1-3, 1-4, and 1-7 to 1-11 below.

The polypeptide described in (b) above has the amino acid sequence of SEQ ID NO: 1 in which one or several amino acid residues are substituted, deleted, inserted, added, and/or inverted (hereinafter sometimes collectively referred to as "mutated", as long as the diaphorase activity is not impaired. The term "several" as used herein indicates a number corresponding to, for example, less than about 20%, preferably less than about 15%, still more preferably less than about 10%, even more preferably less than about 5%, and most preferably less than about 1%, of the total amino acids, although such a number is not limited as long as the diaphorase activity and preferably the properties described in Sections 1-3, 1-4, 1-7 to 1-10 (in particular, Sections 1-3, 1-4, 1-8, and 1-9) below are not impaired. More specifically, the number of mutated amino acid residues is 2 to 127, preferably 2 to 96, more preferably 2 to 64, still more preferably 2 to 32, even more preferably 2 to 20, further preferably 2 to 15, yet further preferably 2 to 10, and most preferably 2 to 5.

The polypeptide described in (c) above is a polypeptide having an amino acid sequence with 80% or more identity to the amino acid sequence of SEQ ID NO: 1, as long as diaphorase activity and preferably the properties described in Sections 1-3, 1-4, and 1-7 to 1-10 above are maintained. The amino acid sequence of the diaphorase of the invention preferably has 85% or more, more preferably 88% or more, still more preferably 90% or more, even more preferably 93% or more, further preferably 95% or more, particularly preferably 98% or more, and most preferably 99% or more, identity to the amino acid sequence of SEQ ID NO: 1. A polypeptide having an amino acid sequence with a specific degree of identity can be produced based on known genetic engineering techniques mentioned above.

Alternatively, the diaphorase of the present invention preferably comprises any one of the following polypeptides (a) to (c):

(a) a polypeptide having the amino acid sequence of SEQ ID NO: 4, (b) a polypeptide having the amino acid sequence of SEQ ID NO: 4 in which one or several amino acid residues are substituted, deleted, inserted, added, and/or inverted at a site other than position 122, and having diaphorase activity, and (c) a polypeptide having an amino acid sequence with 80% or more identity to the amino acid sequence of SEQ ID NO: 4, wherein the glycine at position 122 in SEQ ID NO: 4 is modified to aspartic acid, and having diaphorase activity.

The polypeptide having the amino acid sequence of SEQ ID NO: 4, wherein the glycine at position 122 in the amino acid sequence of SEQ ID NO: 1 is modified to aspartic acid. The polypeptide exhibits all of the properties described in Sections 1-3 to 1-10 below.

As shown in Example 6, the amino acid sequence of SEQ ID NO: 1 is equal to the amino acid sequence of a diaphorase derived from *Geobacillus* sp. Y4.1MC1.

The polypeptide described in (b) above has the amino acid sequence of SEQ ID NO: 4 in which one or several amino acid residues are substituted, deleted, inserted, added, and/or inverted (hereinafter sometimes collectively referred to as "mutated") at a site other than position 122, as long as diaphorase activity is not impaired.

The term "several" as used herein indicates a number corresponding to, for example, less than about 20%, preferably less than about 15%, still more preferably less than about 10%, even more preferably less than about 6%, yet further preferably less than about 5%, and most preferably less than about 1%, of the total amino acids, although such a number is not limited as long as the diaphorase activity and preferably the properties described in Sections 1-3 to 1-11 below are not impaired. More specifically, the number of mutated amino acid residues is 2 to 127, preferably 2 to 96, more preferably 2 to 64, still more preferably 2 to 32, even more preferably 2 to 20, further preferably 2 to 15, yet further preferably 2 to 10, and most preferably 2 to 5.

When the muation is an amino acid substitution, the type of amino acid substitution is not particularly limited, but is preferably a conservative amino acid substitution, because this would not cause a significant effect on the phenotype of diaphorase. The "conservative amino acid substitution" refers to a replacement of an amino acid residue with another amino acid residue having a side chain with similar properties. Amino acid residues are grouped into various families according to their side chains, such as basic side chains (e.g., lysine, arginine, and histidine), acidic side chains (e.g., aspartic acid and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, tryptophan, and histidine). The conservative amino acid substitution is preferably a replacement between amino acid residues of the same family.

One or more mutations can be performed by introducing one or more mutations into the DNA encoding the diaphorase of the present invention as described below by using known techniques, such as restriction enzyme treatment, treatment with exonuclease, DNA ligase, or the like, a site-directed mutagenesis induction method (Molecular Cloning, Third Edition, Chapter 13, Cold Spring Harbor Laboratory Press, New York), a random mutagenesis introduction method (Molecular Cloning, Third Edition, Chapter 13, Cold Spring Harbor Laboratory Press, New York), and the like. Other methods, such as ultraviolet irradiation, may also be used to produce a variant diaphorase. Variant diaphorases also include naturally occurring variants (e.g., a single nucleotide polymorphism), for example, based on the individual variability of microorganisms carrying the diaphorase, or on differences in the species or families of those microorganisms.

In terms of the modified diaphorase of the present invention, the pre-modified "wild-type diaphorase" is not particularly limited. Examples include those derived from microorganisms as described later in Section 1-11, etc., and modifications thereof.

Also, in the modified diaphorase of the present invention, the "site other than position 122" is not particularly limited. Examples thereof include at least one site selected from the group consisting of those corresponding to positions 65, 96, 117, 120, 130, 133, 150, 167 and 168, which are modification sites of the diaphorase derived from *Bacillus stearothermophilus* disclosed in Patent Document 8.

In terms of maintaining the diaphorase activity, the one or more mutations above are preferably present in sites that do not influence the diaphorase active site or substrate binding site.

The polypeptide described in (c) above is a polypeptide having an amino acid sequence with 80% or more identity to the amino acid sequence of SEQ ID NO: 4, as long as the diaphorase activity and preferably at least one property from among the properties described in Sections 1-3 to 1-11 above are maintained. The polypeptide described in (c) has an amino acid sequence in which the glycine at position 122 is modified to aspartic acid in the alignment of SEQ ID NO: 4.

The amino acid sequence of the diaphorase of the invention preferably has 85% or more, more preferably 88% or more, still more preferably 90% or more, even more preferably 93% or more, yet more preferably 94% or more, further preferably 95% or more, particularly preferably 98% or more, and most preferably 99% or more, identity to the amino acid sequence of SEQ ID NO: 4. A polypeptide having an amino acid sequence with a specific degree of identity can be produced based on known genetic engineering techniques mentioned above.

The amino acid sequence identity can be calculated using a commercially available analytical tool or an analytical tool available through telecommunication (Internet). For example, the online homology algorithm Basic Local Alignment Search Tool (BLAST) of the National Center for Biotechnology Information (NCBI), available at http://www.ncbi.nlm.nih.gov/BLAST/, may be used for the calculation using parameters with default (initial) settings. In this specification, the amino acid sequence identity is calculated with this method.

1-3. Temperature Stability

In this specification, when 50 U/mL of purified enzyme that has been treated for 60 minutes in an appropriate buffer solution (e.g., potassium acetate buffer (pH of 7.5)) under specific temperature conditions has remaining enzyme activity that is not substantially reduced compared to the enzyme activity of the same enzyme before treatment (i.e., when about 80% or more of the enzyme activity remains), the enzyme is considered to be stable under these temperature conditions. The diaphorase of the invention is preferably stable at a temperature range of 0 to 70° C.

The diaphorase of the present invention is preferably stable under at least the temperature range of 0 to 70° C. When the enzyme after being treated under the conditions described above maintains enzyme activity of about 90% or more and is considered to be temperature stable, the diaphorase of the present invention is preferably stable at a temperature range of 0 to 60° C.

Alternatively, when the treatment time is 15 minutes and the enzyme after being treated maintains enzyme activity of about 90% or more and is considered to be temperature stable, the diaphorase of the present invention is preferably stable at a temperature range of 0 to 70° C.

1-4. Affinity for NADH

The diaphorase of the invention preferably has high affinity for NADH. Due to this high affinity, even when a sample contains NADH at a low concentration, the catalytic reaction described above can proceed. Further, such high affinity contributes to a more accurate measurement of the diaphorase concentration, measurement in a shorter period of time, and measurement with the use of a smaller amount of enzyme. The affinity of diaphorase for NADH is expressed as a Km value. The Km value is calculated from a so-called Michaelis-Menten equation. Specifically, the Km value is calculated by varying the NADH concentration in the activity measurement method described in Section 1-1 above, and measuring the activity in each concentration to create a Lineweaver-Burk plot.

According to enzyme kinetics, an enzyme having a lower Km value has a higher affinity for a substrate, and the enzyme can form a complex with the substrate even at a low substrate concentration, allowing the catalytic reaction to proceed at a faster rate.

The diaphorase of the invention of Item 1, Item 2, Item A or Item B has a Km value for NADH of preferably 1 mM or less, more preferably 0.5 mM or less, still more preferably 0.3 mM or less, even more preferably 0.1 mM or less, and further preferably 0.08 mM or less.

The diaphorase of the invention of Item 3, Item 4, Item 5, Item D, Item E, Item F or Item G has a Km value for NADH of preferably 1.5 mM or less, more preferably 1.0 mM or less, still more preferably 0.8 mM or less, even more preferably 0.5 mM or less, and further preferably 0.4 mM or less.

1-5. Inhibition of Enzymatic Reaction of Diaphorase Under the Presence of High-Concentration NADH The variant diaphorase of the present invention exhibits reduced inhibition to diaphorase enzymatic reaction under the presence of a high concentration of NADH compared to wild-type diaphorase. When the specific activity under the presence of 20 mM NADH is taken as 100%, the variant diaphorase of the present invention preferably maintains specific activity of 90% or more and/or maintains specific activity of 50% or more in the presence of 80 mM NADH.

The extent of inhibition can be indicated by measuring the rate of the enzymatic reaction proceeding under the conjugation of NADH and a mediator. More specifically, the extent of inhibition can be obtained, while changing the concentration of NADH in the method for measuring diaphorase activity described in Section 1-1-2 above, by measuring the activity at each concentration.

The enzyme activity of the diaphorase of the present invention under the presence of a high concentration of NADH is preferably 450 U/mg or more at 40 mM NADH, more preferably 500 U/mg or more, still more preferably 550 U/mg or less, even more preferably 580 U/mg or more, and particularly preferably 600 U/mg or more.

As described above, the diaphorase of the present invention has excellent affinity for the substrate (NADH) and temperature stability, allowing a reduction of the addition amount thereof compared to other diaphorases when applied to various products.

Theoretically, even if the affinity for the substrate is low, or the temperature stability is slightly unfavorable, when the enzyme amount is increased, desirable diaphorase performance may be obtained. However, for example, when the enzyme is applied to a chip in a dry form, such as an enzyme sensor, the more the addition amount increases, the more the solids content increases. This may hinder the uniform diffusion of a small amount of blood sample on the sensor, adversely affecting the precision of the measurement. In addition, the impurity, which did not cause a problem when the amount was small, may adversely affect the measurement or reaction as its addition amount increases. However, such problems can be prevented by using the diaphorase of the present invention.

Furthermore, using the diaphorase of the present invention prevents problems such as the inability to increase the addition amount of NADH (i.e., the substrate) in fuel cells, which makes it difficult to obtain satisfactory electromotive force or product life.

The variant diaphorases are not particularly limited and the preferable examples thereof include those described in Item 3, Item 4, Item 5, Item D, Item E, Item F or Item G.

1-6. Temperature Dependence

The variant diaphorase of the present invention has improved (i.e., reduced) temperature dependence compared to wild-type diaphorase. In the present invention, temperature dependence means that the enzyme activity changes depending on changes in temperature. Improvement in temperature dependence means that the change in the enzyme activity is slight and a fixed enzyme activity can be observed across a wide temperature range.

In the claims of the present invention, "the improvement in the temperature dependence" is determined based on the following method.

(1) Measuring the activity value (U/ml) at 37° C. after treatment for 24 hours, and taking the measured value as A.

(2) Measuring the activity value (U/ml) at 25° C. after treatment for 24 hours, and taking the measured value as B.

(3) Measuring the relative value (%) of B when A is taken as 100% to define the "temperature dependence."

(4) When the relative value (%) is large, the temperature dependence is determined to be good. Accordingly, when the relative value (%) of the wild-type enzyme (WT) is smaller than that of the modified enzyme, the temperature dependence is determined to be improved.

The above calculation is employed to perform a comparison when the value of B does not exceed the value of A. When the value of B exceeds the value of A, the smaller the relative value (%) of B, when A is taken as 100%, the better the temperature dependence. When the relative value (%) of the wild-type enzyme (WT) is greater than the modified enzyme, the temperature dependence is determined to be improved. When the two cases, "the value of B does not exceed the value of A" and "the value of B exceeds the value of A," are compared, the case where the absolute value of the difference between A and B is smaller is determined to have better temperature dependence. When the absolute value of the difference between A and B in the wild-type enzyme (WT) is greater than that in the modified enzyme, it is determined that the temperature dependence was improved.

When DCPIP is used as a mediator and the activity value at 37° C. is taken as 100%, the relative activity at 25° C. is preferably 70% or more. When a naphthoquinone derivative is used as a mediator and the activity value at 37° C. is taken as 100%, the relative activity at 25° C. is preferably 50% or more.

When the activity value at 30° C. is taken as 100%, the variant diaphorase of the present invention preferably has relative activity at 25° C. of 90% or more. When a naphthoquinone derivative is used as a mediator and the activity value of the variant diaphorase of the present invention at 30° C. is taken as 100%, the relative activity at 25° C. is preferably 90% or more. More specifically, the diaphorase of the present invention exhibits, in particular, reduced temperature dependence in a temperature range of 25 to 30° C., which is close to room temperature.

When a naphthoquinone derivative is used as a mediator, the variant diaphorase of the present invention more preferably has a specific activity of 1.5 times that of a wild-type diaphorase in the temperature range of 25 to 37° C.

The variant diaphorase is not particularly limited and a preferable example thereof includes the diaphorase of Item 3, Item 4, Item 5, Item D, Item E, Item F or Item G.

1-7. Optimal Activity pH

The diaphorase of the present invention of Item 1, Item 2, Item A or Item B preferably exhibits the highest activity at pH of 7.3 (potassium phosphate buffer solution), as described in the Examples. Furthermore, at pH of 6.5 to 8.0 (potassium phosphate buffer solution) and pH of 7.5 to 8.0 (Tris HCl buffer solution), the diaphorase of the present invention preferably exhibits relative activity of 80% or more when the activity at pH of 7.3 (potassium phosphate buffer solution) is taken as 100%. More specifically, the optimal activity pH of the diaphorase of the present invention is 6.7 to 8.0, and preferably 7.3.

The diaphorase of the present invention of Item 3, Item 4, Item 5, Item D, Item E, Item F or Item G preferably exhibits the highest activity at pH of 7.9 (potassium phosphate buffer solution), as described in the Examples. Furthermore, at pH of 7.5 to 8.0 (TrisHCl buffer solution) and at pH of 6.5 to 8.0 (potassium phosphate buffer solution), the diaphorase of the present invention preferably exhibits 60% or more relative activity when the activity at pH of 7.9 (potassium phosphate buffer solution) is taken as 100%. More specifically, the optimal activity pH of the diaphorase of the present invention is in the range of 6.5 to 8.0, more preferably 6.8 to 8.0 at which 80% or more relative activity is exhibited, and even more preferably pH of 7.9.

1-8. pH Stability

In this specification, when a 25 U/mL enzyme that has been treated for 16 hours under specific pH conditions maintains about 95% or more of the enzyme activity compared to the enzyme activity before treatment, the enzyme is considered to be stable under these pH conditions. The diaphorase of the invention is preferably stable at least within the entire pH range of 5.0 to 9.0.

The diaphorase of the present invention of Item 1, Item 2, Item A or Item B preferably has at least one, more preferably 2 or more, still more preferably 3 or more, and particularly preferably all of the properties described in Sections 1-3, 1-4, 1-7 and 1-8. The diaphorase of the present invention may have any combination of the properties described in Section 1-3, 1-4, 1-7 or 1-8.

The diaphorase of the present invention of Item 3, Item 4, Item 5, Item D, Item E, Item F or Item G preferably has at least one, more preferably 2 or more, still more preferably 3 or more, even more preferably 4 or more, further preferably 5 or more, yet further preferably 6 or more, and particularly preferably all, of the properties described in Sections 1-3 to 1-8 above. The diaphorase of the present invention may have any combination of the properties described in Sections 1-3 to 1-8 above.

The pH stability, optimal activity pH, and other properties of the diaphorase of the present invention include an acceptable allowance to some extent.

1-9. Molecular Weight of Subunit

The polypeptide moiety constituting the diaphorase of the invention preferably has a molecular weight of about 23.7 kDa as measured by SDS-PAGE. The "about 23.7 kDa" includes a range in which a person skilled in the art would usually determine that the band is present at a position of 23.7 kDa when molecular weight is measured by SDS-PAGE. The "polypeptide moiety" refers to a diaphorase substantially not having an attached sugar chain.

The molecular weight measurement by SDS-PAGE may be performed using general techniques and devices with the use of commercially available molecular weight markers.

1-10. Molecular Weight of Composite

The molecular weight of the polypeptide moiety constituting the diaphorase of the invention of Item 1, Item 2, Item A or Item B is preferably about 53.3 kDa when measured by gel filtration. About "53.3 kDa" includes a range in which a person skilled in the art would usually determine that the retention time is present at a position of 53.3 kDa when the molecular weight is measured by gel filtration. The "polypeptide moiety" refers to a diaphorase substantially not having an attached sugar chain.

The molecular weight of the polypeptide moiety constituting the diaphorase of the invention of Item 3, Item 4, Item 5, Item D, Item E, Item F or Item G is preferably about 55.3 kDa when measured by gel filtration.

The molecular weight measurement by gel filtration may be performed using general techniques and devices with the use of commercially available molecular weight markers.

The diaphorase of the present invention of Item 3, Item 4, Item 5, Item D, Item E, Item F or Item G is preferably a homo-dimer having a molecular weight of about 55,300 Da with a subunit having a molecular weight about 23,700 Da forming a dimer.

1-11. Origin

The origin of the diaphorase of the present invention is not particularly limited as long as it has the properties described above. The diaphorase of the present invention may originate from microorganisms that belong to the genus *Geobacillus*. Examples of the microorganisms belonging to the genus *Geobacillus* include *Geobacillus stearothermophilus*, *Geobacillus kaustophilus* HTA426, *Geobacillus thermoleovorans*, *Geobacillus thermoglucosidasius*, *Geobacillus caldoxylosilyticus*, *Geobacillus tepidamans*, *Geobacillus toebii* subsp. *decanicus*, *Geobacillus galactosidasius*, *Geobacillus* sp. Y412MC61, *Geobacillus* sp. Y412MC52, *Geobacillus* sp. G11MC16, *Geobacillus* sp. Y4.1MC1, *Geobacillus zalihae*, and *Geobacillus thermodenitrificans*. More specifically, *Geobacillus* sp. Y4.1MC1 can be exemplified. *Geobacillus* sp. Y4.1MC1 is maintained in the American Type Culture Collection (ATCC), and can be obtained after completing predetermined procedures.

Examples of other organisms from which the diaphorase of the invention is derived include microorganisms living in soils, rivers, lakes, and other water systems or in oceans; microorganisms indigenously present in the surface of or inside various animals or plants, and the like. As an isolation source, it is also possible to use microorganisms that thrive in low-temperature environments; high-temperature environments such as volcanoes; anoxic, high-pressure, and aphotic environments such as deep seas; and special environments such as oil fields.

In addition to diaphorases directly isolated from microorganisms, the diaphorase of the invention also includes diaphorases obtained through protein engineering methods by which the amino acid sequence, etc., of an isolated diaphorase has been modified, or diaphorases obtained through genetic engineering techniques by which the isolated diaphorase has been modified. Examples of usable diaphorases include those obtained from enzymes derived from microorganisms of the family Bacillaceae, more specifically, from the genus *Geobacillus*, the enzymes having been modified to have the properties described above. Specific examples thereof include those derived from the following microorganisms and modified to have the above properties. Specific examples thereof include the genus *Geobacillus stearothermophilus*, *Geobacillus kaustophilus* HTA426, *Geobacillus thermoleovorans*, *Geobacillus thermoglucosidasius*, *Geobacillus caldoxylosilyticus*, *Geobacillus tepidamans*, *Geobacillus toebii* subsp. *decanicus*, *Geobacillus galactosidasius*, *Geobacillus* sp. Y412MC61, *Geobacillus* sp. Y412MC52, *Geobacillus* sp. G11MC16, *Geobacillus* sp. Y4.1MC1, *Geobacillus zalihae*, and *Geobacillus thermodenitrificans*.

2. DNA Encoding Diaphorase

The DNA of the present invention encodes the diaphorase of Item 1 above and specifically one of the following (A) to (F).

(A) DNA encoding the amino acid sequence of SEQ ID NO: 1, (B) DNA having the base sequence of SEQ ID NO: 2, (C) DNA having a base sequence with 80% or more homology to the base sequence of SEQ ID NO: 2, and encoding a polypeptide having diaphorase activity, (D) DNA hybridizing to a base sequence complementary to the base sequence of SEQ ID NO: 2 under stringent conditions, and encoding a polypeptide having diaphorase activity, (E) DNA encoding a polypeptide having the amino acid sequence of SEQ ID NO: 2 in which one or several bases are substituted, deleted, inserted, added, and/or inverted, and encoding a polypeptide having diaphorase activity, and (F) DNA encoding a polypeptide having the amino acid sequence of SEQ ID NO: 1 in which one or several amino acid residues are substituted, deleted, inserted, added, or inverted, and having diaphorase activity.

The DNA of the invention may be DNA hybridizing to a base sequence complementary to the base sequence of SEQ ID NO: 2 under stringent conditions, as long as the protein coded by this DNA has diaphorase activity and preferably at least one property from among the properties described in Sections 1-2 to 1-4 and 1-7 to 1-11 above.

Alternatively, the DNA of the present invention encodes the diaphorase of Item 1 above, and specifically one of the following.

(A) DNA encoding the amino acid sequence of SEQ ID NO: 4, (B) DNA having the base sequence of SEQ ID NO: 5, (C) DNA having a base sequence with 80% or more homology to the base sequence of SEQ ID NO: 5, in the alignment of SEQ ID NO: 5, a triplet at positions 364 to 366 encoding an aspartic acid, and encoding a polypeptide having diaphorase activity, (D) DNA hybridizing to a base sequence complementary to the base sequence of SEQ ID NO: 5 under stringent conditions, in the alignment of SEQ ID NO: 5, a triplet at positions 364 to 366 encoding an aspartic acid, and encoding a polypeptide having diaphorase activity, (E) DNA encoding a polypeptide having the amino acid sequence of SEQ ID NO: 5 in which one or several bases are substituted, deleted, inserted, added, and/or inverted, wherein, a triplet at positions 364 to 366 in the alignment with SEQ ID NO: 5 encodes an aspartic acid, and wherein the DNA encodes a polypeptide having diaphorase activity, and (F) DNA encoding a polypeptide having the amino acid sequence of SEQ ID NO: 4 in which one or several amino acid residues are substituted, deleted, inserted, added, or inverted at a position other than position 122, and having diaphorase activity.

The DNA of the invention may be DNA hybridizing to a base sequence complementary to the base sequence of SEQ ID NO: 5 under stringent conditions, as long as a triplet at positions 364 to 366 in the alignment of SEQ ID NO: 5 encodes an aspartic acid, and the protein encoded by this DNA has diaphorase activity and preferably at least one property from among properties described in Sections 1-2 to 1-11 above.

As used herein, the phrase "DNA encoding a protein" refers to DNA from which the protein is obtained when the DNA is expressed. Specifically, the "DNA encoding a protein" refers to DNA having a base sequence corresponding to the amino acid sequence of the protein. Therefore, the "IA encoding a protein" also includes DNA that varies according to codon degeneracy.

The base sequence homology (identity) can be calculated using a commercially available analytical tool or an analytical tool available through telecommunication (Internet). For example, software, such as FASTA, BLAST, PSI-BLAST, or SSEARCH, is used for the calculation. Specifically, the main initial conditions generally used in a BLAST search are as follows: in Advanced BLAST 2.1, a blastn program is used, and the parameters are taken as default values to perform a search to thereby obtain the homology value (%) of a nucleotide sequence. Here, this method is used for calculating the identity of base sequences.

The "stringent conditions" as used herein refer to conditions under which a specific hybrid is formed, while a non-specific hybrid is not formed. Such stringent conditions are known to a person skilled in the art and may be established with reference to, for example, Molecular Cloning (Third Edition, Cold Spring Harbor Laboratory Press, New York) or Current Protocols in Molecular Biology (edited by Frederick M. Ausubel et al., 1987).

Examples of specific stringent conditions include conditions in which a hybridization solution (50% formamide, 10×SSC (0.15 M NaCl, 15 mM sodium citrate, pH of 7.0), 5×Denhardt's solution, 1% SDS, 10% dextran sulfurate, 10 µg/mL of denatured salmon sperm DNA, and 50 mM phosphoric acid buffer (pH of 7.5)) is used, and incubation is carried out at about 42 to 50° C., followed by washing at about 65 to 70° C. with 0.1×SSC and 0.1% SDS. More preferable examples of stringent conditions include conditions in which 50% formamide, 5×SSC (0.15 M NaCl, 15 mM sodium citrate, pH of 7.0), 1×Denhardt's solution, 1% SDS, 10% dextran sulfate, 10 µg/mL of denatured salmon sperm DNA, and 50 mM phosphoric acid buffer (pH of 7.5) are used as a hybridization solution. In the present invention, the stringent conditions indicated the conditions described above.

DNA that undergoes hybridization under the above conditions possibly includes DNA containing a stop codon in the middle, or DNA whose activity is abolished as a result of the mutation in the active center. However, such DNA can be easily removed by introducing it into a commercially available active expression vector, expressing it in a suitable host, and determining the enzyme activity using known techniques.

Regarding the number of DNA mutations, the term "several" as used herein is the same as that described in Section 1-2 above. Specifically, the term indicates a number corresponding to, for example, less than about 20%, preferably less than about 15%, still more preferably less than about 10%, even more preferably less than about 6%, furthermore preferably less than about 5%, and most preferably less than about 1%, of the total amino acids, although such a number is not limited as long as the diaphorase activity and preferably the properties described in Sections 1-3 to 1-11 above are not impaired. More specifically, for example, the number is 2 to 382, preferably 2 to 286, more preferably 2 to 290, still more preferably 2 to 95, even more preferably 2 to 19, further preferably 2 to 15, yet further preferably 2 to 10, and most preferably 2 to 5.

In a preferable embodiment, DNA encoding the diaphorase of the invention is present in an isolated state. As used herein, DNA in an "isolated" state means that the DNA is separated from components such as other nucleic acids and proteins that coexist in nature. However, it is possible for the DNA to contain a portion of other nucleic acid components, such as nucleic acid sequences (e.g., promoter region sequences and terminator sequences) that naturally flank the DNA sequence. For example, chromosomal DNA in an isolated state is preferably substantially free of other DNA components coexisting in nature. When DNA prepared by genetic engineering techniques, such as DNA molecules, is in an isolated state, it is preferably substantially free of cell components, culture media, and the like. Likewise, when DNA prepared by chemical synthesis is in an isolated state, it is preferably substantially free of precursors (starting materials) such as dNTP, as well as chemical substances, etc., used in the synthetic process. When referred to simply as "DNA" in this specification, it means that the DNA is in an isolated state, unless it is otherwise clearly stated that it has a different meaning. The DNA of the invention includes DNA (cDNA) complementary to the DNAs described in (A) to (F) above. The DNA of the invention also includes recombinant DNA.

The DNA of the invention may be produced or obtained by chemical DNA synthesis based on this specification or the sequence information (in particular SEQ ID NO: 2 or SEQ ID NO: 5) in the accompanying Sequence Listing. It is also possible to easily prepare the DNA of the invention by using standard genetic engineering techniques, molecular biological techniques, biochemical techniques, and the like (see Molecular Cloning 2nd Ed, Cold Spring Harbor Lab. Press (1989); *Zoku-Seikagaku Jikken Kouza, Idenshi Kenkyuho* I, II, III, [Sequel Biochemical Experiment Lecture, Gene Study Methods I, II, III], 1986, Japanese Biochemical Society ed.; etc.). Examples of chemical DNA synthesis include solid-phase synthesis using a phosphoramidite method. An automated synthesis device may be used in this synthesis.

Standard genetic engineering techniques can be performed, specifically, by preparing a cDNA library from suitable source microorganisms that can express the diaphorase of the invention according to a known method, and selecting desired clones using an appropriate probe or antibody specific to the DNA sequence of the invention (e.g., the base sequence of SEQ ID NO: 2) from this library (Proc. Natl. Acad. Sci., U.S.A., 78, 6613; (1981) Science 122, 778 (1983), etc.).

The source microorganisms for preparing a cDNA library are not limited, as long as they express the diaphorase of the invention, but are preferably microorganisms of the genus *Geobacillus*. A preferable example of *Geobacillus* species suitable as source microorganisms includes *Geobacillus* sp. Y4.1MC1.

Separation of total RNA from the above microorganisms, separation and purification of mRNA, production and cloning of cDNA, and the like, may all be carried out using known methods. Methods for screening cDNA libraries for the DNA of the invention are also not limited and can be performed using usual methods. For example, a method may be used in which immunological screening is performed by using antibodies specific to a polypeptide derived from cDNA to select the corresponding cDNA clones. It is also possible to use a plaque hybridization method or a colony hybridization method using probes that selectively bind to the target nucleotide sequence. Combinations of these methods may also be used.

In obtaining DNA, it is preferable to use PCR (Science 130, 1350 (1985)) or modified versions of PCR, such as DNA or RNA amplification methods. If obtaining full-length cDNA from libraries is difficult, it is preferable to use a RACE method (Rapid amplification of cDNA ends; *Jikken Igaku* [Experimental medicine], 12 (6), 35 (1994)), in particular, a 5'-RACE method (M. A. Frohman, et al., Proc. Natl. Acad. Sci., U.S.A., 8, 8998 (1988)), or the like.

The primers used in PCR may also be suitably designed and synthesized based on the base sequence of SEQ ID NO: 2 or SEQ ID NO: 5. As described above, amplified DNA or RNA fragments may be isolated and purified according to known methods, such as gel electrophoresis and hybridization.

The use of the DNA of the invention enables easy and stable production of the diaphorase of the invention in large amounts.

3. Vector

The vector of the invention contains the DNA encoding the diaphorase of the invention described in Section 2 above. The "vector" as used herein is not particularly limited in terms of type and structure, insofar as it is a nucleic acid molecule (carrier) that can transfer an inserted nucleic acid molecule to a target such as a cell, replicate the DNA of the invention in a suitable host cell, and express the DNA of the invention. Specifically, the vector of the invention is an expression vector. An appropriate type of vector is selected in consideration of the type of host cell. Specific examples of vectors include plasmid vectors, cosmid vectors, phage vectors, viral vectors (e.g., adenoviral vectors, adeno-associated viral vectors, retroviral vectors, herpes viral vectors), and the like. Vectors suitably used when filamentous fungi are used as hosts may also be used. It is also possible to use vectors suitable for self-cloning.

In the use of *Escherichia coli* as a host, for example, an M13 phage or modifications thereof, a λ phage or modifications thereof, and pBR322 or modifications thereof (e.g., pB325, pAT153, pUC8) may be used. In the use of yeast as a host, pYepSec1, pMFa, pYES2, and the like, may be used. In the use of insect cells as a host, for example, pAc and pVL may be used. In the use of mammalian cells as a host, for example, pCDM8 and pMT2PC may be used. However, the vectors are not limited to these examples.

An expression vector usually contains, for example, a promoter sequence required for expression of an inserted nucleic acid, and an enhancer sequence for facilitating the expression. It is also possible to use an expression vector containing a selection marker. In the use of such an expression vector, the expression vector introduction (and the degree of the introduction) can be confirmed using the selection marker. Insertion of the DNA of the invention into a vector, insertion of a selection marker gene (if required), insertion of a promoter (if required), and the like, may be performed using standard recombinant DNA technology (e.g., well-known methods that use restriction enzymes and DNA ligase, with reference to Molecular Cloning, Third Edition, 1.84, Cold Spring Harbor Laboratory Press, New York).

4. Transformant

The present invention also relates to a transformant obtained by introducing the DNA of the invention into a host cell. The means for introducing the DNA of the invention into a host cell is not particularly limited. For example, the DNA contained in a vector described in Section 3 above may be introduced into a host cell. Host cells are not particularly limited as long as they can express the DNA of the invention to produce a diaphorase.

Specifically, it is possible to use prokaryotic cells, such as *Escherichia coli* and *Bacillus subtilis*; and eukaryotic cells, such as yeast, mold, insect cells, and mammal cells.

When *Escherichia coli* is used as the host, a K-12 derived strain is particularly preferable. Examples of *Escherichia coli* used as a host include BL21(DE3), BB4, BM25.5, BMH71-18mutS, BW313, C-la, C600, CJ236, DH1, DH5, DH5α, DH10B, DP50supF, ED8654, ED8767, ER1647, HB101, HMS174, HST02, HST04dam-/dcm-, HST08 Premium, JM83, JM101, JM105, JM106, JM107, JM108, JM109, JM110, K802, K803, LE392, MC1061, MV1184, MV1193, NovaBlue, RR1, TAP90, TG1, TG2, TH2, XL1-Blue, X-1776, γ-1088, γ-1089, and γ-1090. Examples of vectors include pBR322, pUC19, pUC57, pBluescript, pET22b, pUC18, pHSG398, pHSG399, pRIT2T, pUEX1-3, pKK223-3, pINIII 1, pTTQ18, pGEMEX-1, pGH-L9, and pKK233-2.

Examples of *Bacillus subtilis* used as a host include *Bucillus subtilus*, *Brevibacillus brevis*, and *Brevibacillus choshinensis*. Examples of the vectors include pTB53 or modifications thereof, pHY300PLK or modifications thereof, pAL10, pAL12, pHT01, pHT08, pHT09, pHT10, pHT43, pNY326, and pNCMO2.

Examples of yeast used as a host include *Saccharomyces cerevisiae, Schizosaccharomyces pombe, Candida utilis, Pichia pastoris*, and the like, and examples of the vectors include pAUR101, pAUR224, pYE32, and the like.

Examples of filamentous fungal cells used as a host include Aspergillusoryzae. Additionally, as a host, it is also preferable to use microorganisms that belong to the genus *Geobacillus* from which the diaphorase is isolated. Specifically, although in transformants, foreign DNA is generally present in a host cell, a preferable embodiment also includes transformants obtained by self-cloning in which microorganisms from which the DNA is derived are used as a host.

The transformant of the invention is preferably obtained by transfection or transformation of the expression vector described in Section 3 above. The transformation may be a transient or stable transformation. Transfection or transformation may be performed by a calcium phosphate co-sedimentation method, an electroporation method (Potter, H. et al., Proc. Natl. Acad. Sci. U.S.A. 81, 7161-7165 (1984)), a lipofection method (Felgner, P. L. et al., Proc. Natl. Acad. Sci. U.S.A. 84, 7413-7417 (1984)), a microinjection method (Graessmann, M. & Graessmann, A., Proc. Natl. Acad. Sci. U.S.A. 73, 366-370 (1976)), a Hanahan method (Hanahan, D., J. Mol. Biol. 166, 557-580 (1983)), a lithium acetate method (Schiestl, R. H. et al., Curr. Genet. 16, 339-346 (1989)), a protoplast-polyethylene glycol method (Yelton, M. M. et al., Proc. Natl. Acad. Sci. 81, 1470-1474 (1984)), or the like.

The transformant of the invention is capable of producing the diaphorase of the invention. Therefore, the use of the transformant of the invention enables efficient production of the diaphorase of the invention.

5. Method for Producing Diaphorase

The diaphorase of the invention is produced by culturing microorganisms that are capable of producing the diaphorase of the invention. Microorganisms to be cultured are not particularly limited, as long as they are capable of producing the diaphorase of the invention. For example, wild-type microorganisms belonging to the genus *Geobacillus* mentioned in Section 1 above, and the transformants described in Section 4 above are preferably used.

Specific examples of microorganisms of the genus *Geobacillus* include: *Geobacillus stearothermophilus*, *Geobacillus kaustophilus* HTA426, *Geobacillus thermoleovorans*, *Geobacillus thermoglucosidasius*, *Geobacillus caldoxylosilyticus*, *Geobacillus tepidamans*, *Geobacillus toebii* subsp. *decanicus*, *Geobacillus galactosidasius*, *Geobacillus* sp. Y412MC61, *Geobacillus* sp. Y412MC52, *Geobacillus* sp. G11MC16, *Geobacillus* sp. Y4.1MC1, *Geobacillus zalihae*, and *Geobacillus thermodenitrificans*.

The microorganisms of the genus *Geobacillus* are maintained in the Biological Resource Center (NBRC), National Institute of Technology and Evaluation (NITE) and American Type Culture Collection (ATCC), and can be obtained after completing predetermined procedures.

The culture method and culture conditions are not limited, as long as the diaphorase of the invention is produced. Specifically, as long as a diaphorase is produced, any method and conditions can be used that are suitable for the growth of the microorganisms to be used. Examples of culture conditions, such as the culture medium, culture temperature, and culture period, are described below.

There is no limitation to the culture media as long as the microorganisms to be used can grow. Examples include those containing carbon sources, such as glucose, sucrose, gentiobiose, soluble starch, glycerin, dextrin, molasses, and organic acids, and further containing ammonium sulfate, ammonium carbonate, ammonium phosphate, and ammonium acetate; those containing nitrogen sources, such as peptone, yeast extract, corn steep liquor, casein hydrolysate, wheat bran, and meat extract; and those containing inorganic salts, such as potassium salts, magnesium salts, sodium salts, phosphoric salts, manganese salts, iron salts, and zinc salts. To promote the growth of the microorganisms, it is also possible to add vitamins, amino acids, etc., to the media.

A commercially available LB medium (Luria-Bertai Medium), M9 medium (M9Minimal Medium), NZCYM medium (NZCYM Medium), NZYM medium (NZYM Medium), NZM medium (NZM Medium), SOB medium (SOB Medium), TB medium (TerrificBroth), and 2XYT medium (2XYT Medium) may be used.

When the diaphorase of the invention is obtained by culturing microorganisms of the genus *Geobacillus*, the culture conditions may be selected in consideration of the nutritional and physiological properties of the microorganisms. Liquid culturing is performed in many cases. Industrially, it is advantageous to perform aeration-agitation culturing. In terms of productivity, however, performing solid culturing may be more advantageous.

The pH of the medium is not limited as long as it is suitable for the microorganisms to be cultured. The pH value of the medium is adjusted to, for example, about 4 to 9, and preferably about 6 to 8. Culturing is performed at a culture temperature of usually about 10 to 50° C., and preferably about 25 to 35° C., for 1 to 15 days, and preferably about 3 to 7 days, under aerobic conditions. As a culture method, for example, shake culturing or aerobic submerged culturing using a jar fermentor may be used.

It is preferable that the diaphorase is recovered from the culture medium or cells after culturing under the above conditions. When microorganisms that secrete a diaphorase out of the cells are used, the enzyme of the invention can be obtained, for example, in the following manner. Specifically, the culture supernatant is filtered, centrifuged, etc., to remove insoluble matter, and separation and purification are performed by suitably combining the following: ultrafiltration membrane concentration, ammonium sulfate precipitation and other salting out, dialysis, various chromatographies, and the like. A diaphorase produced by microorganisms that belong to the genus *Geobacillus* is basically a secretory protein.

In contrast, when the diaphorase is recovered from inside the cells, the enzyme of the invention can be obtained, for example, in the following manner. Specifically, the cells are disrupted by pressure treatment, ultrasonic treatment, a mechanical technique, or a technique using enzymes such as lysozyme, and a surfactant and a chelating agent such as EDTA are optionally added to solubilize the diaphorase, which is separated and collected as an aqueous solution, followed by separation and purification. It is also possible to perform this series of processes (cell disruption, separation, and purification) after recovering cells in advance from the culture medium by filtration, centrifugation, or the like.

Purification may be performed, for example, by suitably combining vacuum concentration, membrane concentration, salting out with ammonium sulfate or sodium sulfate, fractional precipitation with a hydrophilic organic solvent, such as methanol, ethanol, or acetone, heat treatment, isoelectric focusing, gel filtration with an adsorbent or a gel filtration agent, adsorption chromatography, ion-exchange chromatography, affinity chromatography, and the like.

When column chromatography is used, for example, gel-filtration column chromatography using Sephadex gel (produced by GE Healthcare Bioscience Co., Ltd.) and column chromatography using DEAE Sepharose CL-6B (produced by GE Healthcare Bioscience Co., Ltd.) or Octyl Sepharose CL-6B (produced by GE Healthcare Bioscience Co., Ltd.) may be used. It is preferable that the purified enzyme preparation be purified to the extent that the enzyme migrates as a single band on electrophoresis (SDS-PAGE).

In harvesting (e.g., extracting or purifying) a protein having diaphorase activity from a culture medium, any one or more of the following may be used as indices: diaphorase activity, thermal stability, and the like.

In each purification process, in principle, the diaphorase activity is used as an index for fractionation, thereby proceeding to the next step. This does not apply, however, if the appropriate conditions can be set in advance such as by performing a preliminary test.

To obtain the diaphorase of the invention as a purified preparation, purification is preferably performed to the extent that the specific activity is, for example, the lower limit of 1,000 (U/mg). The lower limit of the specific activity is more preferably 2,000 (U/mg), even more preferably 2,200 (U/mg), and still more preferably 2,400 (U/mg). Furthermore, purification is preferably performed to the extent that the upper limit is 3,000 (U/mg). The upper limit of the specific activity is more preferably 2,800 (U/mg), and even more preferably 2,600 (U/mg). The final form may be either a liquid or a solid (including a powder).

In this specification the term "specific activity" indicates the specific activity measured using DCPIP as a mediator under the conditions described in Section 1-1-1. Measurement Conditions, unless otherwise noted. The term "specific activity" means activity per protein, but depending on the type of solution, the value of A280 may be determined to be the protein concentration to perform a relative comparison.

To obtain the enzyme of the invention as a recombinant protein, various modifications can be made. For example, DNA encoding the enzyme of the invention and other appropriate DNA may be inserted into the same vector, which is used to produce a recombinant protein. In this manner, the enzyme of the invention made of a recombinant protein in which arbitrary peptides or proteins are linked together can be obtained. It is also possible to add sugar chains and/or a lipid, or to make modifications that cause processing at the N-terminus or C-terminus. These modifications make it possible to simplify the extraction and purification of recombinant proteins, and to add biological functions, and the like.

6. Application of the Diaphorase of the Invention

The diaphorase of the present invention is applicable to various kinds of products.

In this specification, the term "product" refers to a product that contains the diaphorase of the invention and that constitutes a part or the whole of one set for a user to accomplish an application described above.

The product of the present invention may be used in various applications without any limitation. Typical examples thereof include those using either of the following two principles:

(a) Measuring a substrate, such as NADH, with a diaphorase.

(b) Generating electric current by an enzymatic reaction using a diaphorase.

Examples of applications using principle (a) above include extracorporeal diagnostics (e.g., measurement of various biological samples). Methods for measuring biogenic substances have already been established in this technical field. The amount or concentration of biogenic substances in various samples can be measured using the diaphorase of the invention according to known methods. The amount and concentration of the biological components in various samples can also be measured using the diaphorase of the present invention.

The mode for the measurement is not limited, as long as the amount and concentration of the biological components are measured using the diaphorase of the present invention. Examples thereof include reagents, kits, sensors and various embodiments for use in measuring glucose, lactate dehydrocenase (LDH), creatine kinase (CK), neutral fat (TG), bile acid, total branched-chain amino acid (BCAA) and like biological components.

LDH can be measured in the following manner. NADH generated by the LDH reaction reduces nitrotetrazolium blue and the like through the diaphorase, and the NADH itself returns to NAD to form a formazan dye. Therefore, the activity value of the LDH can be measured by subjecting the formed formazan dye to colorimetric determination.

Bile acid can also be measured in the same manner. The reaction proceeds while 3-α-hydroxysteroid dehydrogenase uses bile acid as a substrate to produce NADH, and the concentration of bile acid can be measured by performing the colorimetric determination in the same manner as described above.

When BCAA is measured, the reaction also proceeds while leucine dehydrogenase uses BCAA as a substrate to produce NADH, and the concentration of BCAA can be measured by performing the colorimetric determination in the same manner as described above.

When CK is measured, because NADH is not directly produced from the CK reaction, the determination of the CK activity value with diaphorase becomes feasible by designing a so-called coupled reaction described below. That is, the ATP generated by the CK reaction is allowed to react with glucokinase together with the glucose added to the reagent in advance to produce glucose-6-phosphate, and the glucose-6-phosphate is further reacted with glucose-6-phosphate dehydrogenase together with NAD added to the reagent in advance to produce NADH.

When TG is measured, a diaphorase enables the TG concentration to be determined by using a lipoprotein lipase that uses TG as a substrate and by using glycerol dehydrogenase as a coupling enzyme to produce NADH.

By suitably designing such a coupled reaction, the concentration or quantity of biological components other than those described above can be measured.

When glucose is measured, the NADH generated by the glucose dehydrogenase reaction reduces the electron acceptor such as DCPIP through diaphorase, and the NADH itself returns to NAD. By subjecting the difference in absorbance caused by the change in the DCPIP structure to colorimetric determination, the concentration of glucose can be measured. More specifically, the measurement may be performed according to the method described in Section 1-1 above.

The sample containing glucose is not limited. Examples of the samples include blood, beverages, foods, and the like.

The glucose concentration can be measured using a sensor described later, for example, in the following manner. A buffer solution is placed in a thermostated cell, and the temperature is maintained constant. Potassium ferricyanide, phenazine methosulfate, or the like, can be used as a mediator. An electrode on which the diaphorase of the invention is immobilized is used as a working electrode, and a counter electrode (e.g., platinum electrode) and a reference electrode (e.g., Ag/AgCl electrode) are used. A constant voltage is applied across the carbon electrode. After the current becomes constant, a sample containing glucose is added, and the increase in current is measured. The glucose concentration in the sample can be calculated based on the calibration curve prepared from glucose solutions of standard concentration.

Glucose Assay Kit

An embodiment of a kit using the product of the present invention is explained with reference to a glucose assay kit. The glucose assay kit of the invention contains the diaphorase of the invention in an amount sufficient for at least one assay. In addition to the diaphorase of the invention, the kit typically contains a buffer solution and a mediator required for the assay, a glucose standard solution for preparing a calibration curve, and instructions for use. The diaphorase of the invention may be provided in various forms, such as a freeze-dried reagent or a solution in an appropriate storage solution.

Glucose Sensor

An embodiment of a sensor using the product of the present invention is explained with reference to a glucose sensor. In the glucose sensor of the present invention, a carbon electrode, a gold electrode, a platinum electrode, or the like, is used as an electrode on which the enzyme of the invention is immobilized. Examples of immobilization methods include a method using a crosslinking reagent, a method for encapsulating the diaphorase in a polymer matrix, a method for covering the diaphorase with a dialysis membrane, and methods using a photo-crosslinkable polymer, a conductive polymer, a redox polymer, or the like. Alternatively, the diaphorase of the invention may be immobilized in a polymer or immobilized adsorptively onto an electrode, together with an electron mediator, such as ferrocene or its derivative. These methods may also be used in combination. The diaphorase of the present invention exhibits excellent temperature stability and can be immobilized under relatively high-temperature conditions. Typically, the diaphorase of the invention is immobilized on a carbon electrode using glutaraldehyde, followed by treatment with an amine-containing reagent to block the glutaraldehyde.

The glucose concentration can be measured in the following manner. A buffer solution is placed in a thermostated cell, and a constant temperature is maintained. Potassium ferricyanide, phenazine methosulfate, or the like, can be used as a mediator. An electrode on which the diaphorase of the invention is immobilized is used as a working electrode, and a counter electrode (e.g., a platinum electrode) and a reference electrode (e.g., an Ag/AgCl electrode) are used. A constant voltage is applied across the carbon electrode. After the current becomes constant, a sample containing glucose is added, and the increase in current is measured. The glucose concentration in the sample can be calculated based on the calibration curve prepared from glucose solutions of standard concentration.

Examples of applications using principle (b) above include various embodiments such as an enzyme electrode (may be a fixed electrode), an enzyme sensor, a fuel cell, and electronic equipment comprising one or more fuel cells.

Fuel Cell

Fuel cells using glucose dehydrogenase and a diaphorase that extract electrons by an oxidation reaction of glucose have already been established in this technical field. Accordingly, a fuel cell can be produced and operated by a known method using the diaphorase of the present invention.

The embodiments are not limited as long as the fuel cell is produced and operated using the diaphorase of the present invention. For example, the fuel cell can be operated by the means described below. The diaphorase of the present invention is placed on the negative electrode of a biofuel cell and is fixed together with glucose dehydrogenase, osmium complex or a like electron-transfer mediator. On the positive electrode, oxidoreductase selected from bilirubin oxidase (BOD), laccase, ascorbate oxidase and the like, and hexacyanoferrate ion or a like mediator is fixed. Furthermore, the structure may have a negative electrode and a positive electrode facing each other via an electrolyte layer that does not have electronic conductivity and conducts only protons. In this structure, at the negative electrode, glucose supplied as fuel is decomposed by enzymes to extract electrons and, at the same time, protons ($H^+$) are generated. At the positive electrode, protons transported from the negative electrode through the electrolyte layer and electrons transported from the negative electrode through an external circuit react with oxygen, for example, in the air, thereby producing water.

The sample containing glucose is not limited. Examples of samples include blood, beverages, foods, and the like.

Electronic Equipment and the like Comprising Fuel Cell

A fuel cell using the diaphorase of the present invention is applicable to anything that requires electric power, and the size thereof is not limited. More specifically, the fuel cell can be used for objects such as electronic equipment, mobile objects (automobiles, two-wheeled vehicles, aircraft, rockets, spaceships, etc.), power plants, construction machinery, machine tools, power generating systems, and co-generation systems.

The electronic equipment is not limited, and may be, for example, portable or stationary. Examples thereof include, cellular phones, mobile devices, robots, personal computers (including both desktop and notebook types), game machines, camera-integrated VTRs (video tape recorders), in-vehicle equipment, home appliances, and industrial products. Specific examples of the mobile devices include portable digital assistants (PDAs).

The output, size, shape, type of fuel and the like may be suitably selected depending on the target performance, usage, and the like.

Enzyme Electrode (Enzyme Fixed Electrode)

In the fuel cell example above, the diaphorase of the present invention and the like can be fixed to the positive electrode and the negative electrode using a fixing agent comprising, for example, poly-L-lysine (PLL) and glutaraldehyde (GA). The enzyme electrode (enzyme fixed electrode) thus obtained has also already been established in this field. Accordingly, an enzyme electrode (enzyme fixed electrode) can be produced and operated by a known method using the diaphorase of the present invention.

Enzyme Sensor

Production of an enzyme sensor (glucose sensor) for the measurement of glucose using the enzyme electrode (enzyme fixed electrode) obtained above has also already been established in this field. Accordingly, an enzyme sensor (glucose sensor) can be produced and operated by a known method using the diaphorase of the present invention.

When the diaphorase of the present invention is used as a sensor, electrode, fuel cell, or the like, its affinity for the mediator is important. Mediators applicable to the diaphorase of the present invention are not limited, and the relationship between the diaphorase and the mediator is being studied. For example, 2-amino-1,4-naphthoquinone (ANQ), 2-amino-3-methyl-1,4-naphthoquinone (AMNQ), 2-amino-3-carboxy-1,4-naphthoquinone (ACNQ), 2,3-diamino-1,4-naphthoquinone, 4-amino-1,2-naphthoquinone, 2-hydroxy-1,4-naphthoquinone, 2-methyl-3-hydroxy-1,4-naphthoquinone, vitamin K1 (2-methyl-3-phyty-1,4-naphthoquinone), vitamin K2 (2-farnesyl-3-methyl-1,4-naphthoquinone), vitamin K3 (2-methy-1,4-naphthoquinone), and the like are usable as a mediator. Furthermore, examples of the compound having a quinone skeleton include anthraquinone-1-sulfonate, anthraquinone-2-sulfonate and like compounds having a quinone skeleton and derivatives thereof. In particular, derivatives having a naphthoquinone skeleton are inexpensive and safe as a mediator (Patent Document 3, Patent Document 4, Patent Document 5, Patent Document 6, Patent Document 7, Patent Document 9, Patent Document 10, Patent Document 11, Non-patent Document 1, Non-patent Document 4). Accordingly, the diaphorase of the present invention preferably has high reactivity with a mediator having a naphthoquinone skeleton.

The present invention is more specifically described below by presenting Examples.

EXAMPLES

Example 1

Searching for a Homologous Protein

The amino acid sequence (ACCESSION AAD24436) (SEQ ID NO: 3) of the diaphorase of *Geobacillus stearothermophilus* was obtained using the database of the National Center for Biotechnology Information (NCBI). The 211 amino acid residues obtained were analyzed using the protein BLAST algorithm of the National Center for Biotechnology Information (NCBI). As a result, a protein having an amino acid sequence homologous to the amino acid sequence (ACCESSION AAD24436) of the diaphorase of *Geobacillus stearothermophilus* was identified.

Subsequently, amino acid sequences having identities=128/211 (61%) or more in the BLAST search results were excluded. Then, amino acid sequences having identities=126/211 (60%) or less and those derived from thermophilic bacteria were identified. The result revealed that NAD(P)H dehydrogenase (ACCESSION YP_003989131) (SEQ ID NO: 1) of *Geobacillus* sp. Y4.1MC1 had identities=126/211 (60%). Alignment comparison was performed using ClustalW2 (http://www.ebi.ac.uk/Tools/msa/clustalw2/), which is available from the home page of the European Bioinformatics Institute, to clarify the differences in the amino acid sequences (FIG. 1).

Example 2

Acquiring a Gene Encoding the Full-Length Protein

It was necessary to confirm that the NAD(P)H dehydrogenase (ACCESSION YP_003989131) of *Geobacillus* sp. Y4.1MC1 identified in Example 1 was a polypeptide having diaphorase activity. Accordingly, based on the 211 amino acid residues, a synthetic gene having 636 bases (SEQ ID NO: 2) encoding the 211 amino acid residues was designed. In order to facilitate the production of an enzyme protein from *Escherichia coli*, a synthetic gene having a Shine Dalgarno sequence, which is a ribosome binding sequence, added upstream of the initiator methionine was designed in advance. The synthetic gene was synthesized by GenScript Corporation. The synthetic gene supplied from GenScript Corporation was inserted into pUC57, which is a plasmid for cloning vectors.

Example 3

Acquiring a Transformant

The synthetic gene obtained in Example 2 was inserted downstream of the LacZ promoter of pUC57 (i.e., a plasmid). Therefore, the plasmid into which the synthetic gene was inserted was used as the expression vector without modification. This plasmid was named recombinant expression plasmid, pUC-DI-1. Using pUC-DI-1, *Escherichia coli* DH5α-strain competent cells (produced by Toyobo Co., Ltd.) were transformed. After preculturing in the SOC medium at 37° C. for 1 hour, they were developed in an LB-amp agar medium, thereby obtaining a transformant in the form of a colony. The resulting transformant was named *Escherichia coli* DH5α (pUC-DI-1).

Example 4

Inducing Mutation and Acquiring a Transformant (1) Inducing Mutation

A mutation was introduced into the 211 amino acid residues of NAD(P)H dehydrogenase of *Geobacillus* sp. Y4.1MC1 identified in Example 1 and Example 2. The mutation sites were decided according to known information (Non-patent Document 1). Specifically, glycine (the 122nd amino acid) was substituted with aspartic acid (SEQ ID NO: 4)(FIG. 2). In order to confirm that the variant polypeptide thus designed, i.e., NAD(P)H dehydrogenase of 211 amino acid residues, was a polypeptide having diaphorase activity, a synthetic gene of 636 bases encoding 211 amino acid residues in which glycine (i.e., the 122nd amino acid) was substituted with aspartic acid (SEQ ID NO: 5) was designed. To facilitate the production of an enzyme protein from *Escherichia coli*, a synthetic gene having a Shine Dalgarno sequence, which is a ribosome binding sequence, was added upstream of the initiator methionine in advance. Production of the synthetic gene was entrusted to GenScript Corporation. The synthetic gene supplied from GenScript Corporation was inserted into pUC57, which is a plasmid for cloning vectors.

(2) Acquiring a Transformant

The synthetic gene of the variant polypeptide was inserted downstream of the LacZ promoter of pUC57, which is a plasmid. Therefore, the plasmid into which the synthetic gene was inserted was used as the expression vector without modification. This plasmid was named recombinant expression plasmid, pUC-DI-1G122D. Using pUC-DI-1G122D, *Escherichia coli* DH5α-strain competent cells (produced by Toyobo Co., Ltd.) were transformed. After preculturing in the SOC medium at 37° C. for 1 hour, they were developed in an LB-amp agar medium, thereby obtaining the transformant in the form of a colony. The resulting transformant was named *Escherichia coli* DH5α (pUC-DI-1G122D).

Example 5

Preparation of Culture Supernatant

A loopful of the colony of the transformant *Escherichia coli* DH5α (pUC-DI-1) obtained in Example 3 was inoculated in an LB-amp liquid medium in a 5 mL-test tube, followed by culturing at 30° C. for 16 hours. Upon completion of culturing, pUC-DI-1 was collected by centrifugation and suspended in a 50 mM phosphate buffer (pH of 7.5). Thereafter, the result was subjected to ultrasonic fragmentation with a sonicator, followed by further centrifugation. The resulting supernatant was used as a crude enzyme solution. The transformant *Escherichia coli* DH5 (pUC-DI-1G122D) obtained in Example 4 was treated in the same manner to obtain a crude enzyme solution.

Example 6

Comfirmation of Diaphorase Activity

The diaphorase activity in the crude enzyme solution obtained in Example 5 was measured according to the diaphorase activity measurement method described in Section 1-1 above.

The results confirmed the diaphorase activity in the transformant *Escherichia coli* DH5α (pUC-DI-1)-derived crude enzyme solution. This revealed that the synthetic gene is a gene encoding NAD(P)H dehydrogenase of *Geobacillus* sp. Y4.1MC1.

An *Escherichia coli* DH5α (pUC-DI-1G122D) transformant-derived crude enzyme solution was also treated in the same manner to confirm the presence of the diaphorase activity. This revealed that the pUC-DI-1G122D synthetic gene encoding the variant polypeptide had diaphorase activity.

Example 7

Production of *Geobacillus* sp. Y4.1MC1 Derived Wild-Type Diaphorase and Variant Diaphorase (Culturing and Purification)

5 mL of LB liquid medium (trypton 1.0%, yeast extract 0.5%, NaCl 1.0%, pH of 7.0) was placed in a test tube and sterilized in an autoclave, thereby preparing a preculture medium. A loopful of *Escherichia coli* DH5α (pUC-DI-1) transformant, cultured in advance in an LB plate medium, was inoculated in the preculture medium and subjected to shaking culture for 16 hours at 30° C., 180 rpm, thereby obtaining a seed culture solution.

The *Escherichia coli* DH5α (pUC-DI-1G122D) transformant was also treated in the same manner to obtain a seed culture solution.

Using the two types of seed culture solutions obtained above, the following operation was performed. 500 mL TB liquid medium (trypton 1.2%, yeast extract 2.4%, glycerol 0.4%, $KH_2PO_4$ 0.23%, $K_2HPO_4$ 1.25%, pH of 7.0) was placed in a 2-L Sakaguchi flask and sterilized in an autoclave, thereby preparing a main culture medium. 5 mL of the seed culture solution was inoculated in the main culture medium and subjected to shaking culture for 24 hours at 30° C., 180 rpm. Thereafter, the culture solution was subjected to centrifugation to collect the cells. The obtained cells were suspended in a 20 mM potassium phosphate buffer solution (pH of 7.5).

Thereafter, using the two types of suspensions obtained above, the following operation was performed.

The suspension was supplied to a French press (produced by Niro Soavi) at a flow rate of 160 mL/min, and the cells were disrupted at 700 to 1,000 bar. Subsequently, a 5% polyethyleneimine solution (pH of 7.5) was prepared to have an ethyleneimine (polymer) (produced by Nacalai Tesque, Inc.) content of 5%. The solution was gradually added to the disrupted cell solution to have a concentration of 5%, and was stirred at room temperature for 30 minutes. Extra precipitates were removed using a filtration adjuvant. Subsequently, ammonium sulfate (produced by Sumitomo Chemical Co., Ltd.) was gradually added to the disrupted cell solution to give 0.5 saturation, followed by ammonium sulfate fractionation. A protein having diaphorase activity was precipitated and collected. The precipitate of the collected protein was suspended in a 20 mM potassium phosphate buffer solution (pH of 7.5). Thereafter, the suspension was desalted using Sephadex G-25 gel. The resulting liquid was subjected to linear gradient elution with a 20 mM potassium phosphate buffer solution (pH of 7.5) by being passed through a 400 mL DEAE Sepharose Fast Flow column (produced by GE Healthcare Bioscience Co., Ltd.) equilibrated in advance with a 20 mM potassium phosphate buffer solution (pH of 7.5) containing 0.5 M NaCl.

Thereafter, the eluted diaphorase fraction was concentrated using a hollow fiber membrane (produced by Spectrum Laboratories, Inc.) having a molecular weight cutoff of 10,000. The concentrate was desalted using Sephadex G-25 gel, thereby obtaining a purified enzyme.

In the Examples of the present invention, the diaphorase obtained from *Escherichia coli* DH5α (pUC-DI-1) transformant is referred to as "wild-type diaphorase." The diaphorase obtained from *Escherichia coli* DH5α (pUC-DI-1G122D) transformant is referred to as "variant diaphorase."

Using the two types of purified enzyme obtained above, the following operation was conducted.

The resulting purified enzyme was subjected to SDS-polyacrylamide gel electrophoresis (PhastSystem and PhastGel™ Gradient 10-15 PhastSystem: produced by GE Healthcare Bioscience Co., Ltd.). Phosphorylase b (97,000 Da), albumin (66,000 Da), ovalbumin (45,000 Da), carbonic anhydrase (30,000 Da), trypsin inhibitor (20,100 Da), and α-lactalbumin (14,400 Da) were used as protein molecular weight markers.

As the results indicate, the presence of a single band in each enzyme showed that wild-type diaphorase and variant diaphorase were fully purified.

Example 9

Molecular Weight of Subunit

The subunit molecular weight was measured by standard SDS-polyacrylamide gel electrophoresis (PhastSystem and PhastGel™ Gradient 10-15: produced by GE Healthcare Bioscience Co., Ltd.).

The molecular weight of wild-type diaphorase and that of variant diaphorase were obtained based on the mobility of a protein molecular weight marker (Low Molecular Weight Calibration Kit, produced by GE Healthcare Bioscience Co., Ltd.), phosphorylase b: 97,000 Da, albumin: 66,000 Da, ovalbumin: 45,000 Da, carbonic anhydrase: 30,000 Da, trypsin inhibitor: 20,100 Da, α-lactalbumin: 14,400 Da. The results showed that the wild-type diaphorase had a molecular weight of at least about 23,700 Da in a subunit, and the variant diaphorase had a molecular weight of about 23,700 Da in a subunit. FIG. 3(A) shows the results of the wild-type diaphorase, and FIG. 4(A) shows the results of the variant diaphorase.

Example 10

Molecular Weight of Composite

The molecular weight of the enzyme was measured using TSK-gel G3000SW (7.5 mm I.D.×60 cm: produced by Tosoh Corporation). The measurement was performed using a 20 mM potassium phosphate buffer solution (pH of 7) containing 0.15 M NaCl as the buffer solution and at a flow rate of 0.5 mL/min. MW-Marker Protein (HPLC) (produced by Oriental Yeast Co., Ltd.) was used as the protein marker for measuring the molecular weight, thereby determining the molecular weight of the purified enzyme. The molecular weights of the protein markers are shown below. Glutamatedehydrogenase: 290 kDa, lactate dehydrogenase: 142 kDa, enolase: 67 kDa, myokinase: 32 kDa, and ctyochrome C: 12.4 kDa. Under the above described measurement conditions, the retention times of the protein marker and the enzyme were shown below. Glutamatedehydrogenase: 26.47 min, lactate dehydrogenase: 30.44 min, enolase: 35.63 min, myokinase: 38.79 min, ctyochrome C: 44.84 min, wild-type diaphorase: 36.31 min, and variant diaphorase: 36.06 min. The above results confirmed that the molecular weight of the wild-type diaphorase was about 53,300 Da, and that of the variant diaphorase was about 55,300 Da. FIG. 3(B) shows the result of wild-type diaphorase and FIG. 4(B) shows that of a variant diaphorase.

The molecular weight measurement by gel filtration with TSK-gel G3000SW and the measurement by SDS-PAGE revealed that the wild-type diaphorase is a homo-dimer having a molecular weight of about 55,300 Da with a subunit having a molecular weight of about 23,700 Da forming a dimer.
TSK-Gel The molecular weight measurement by gel filtration with G3000SW and the measurement by SDS-PAGE revealed that the variant diaphorase is a homo-dimer having a molecular weight of about 55,300 Da with a subunit having a molecular weight of about 23,700 Da forming a dimer.

Example 11

Optimal Activity pH

The optimal pH was found using the diaphorase enzyme liquid (2 U/mL) obtained in Example 5. A 100 mM potassium phosphate buffer solution (pH of 6.0 to 8.0, plotted with black ♦ diamond shapes in the figure), a 100 mM Tris-HCl buffer solution (pH of 7.5 to 9.0, plotted with black ■ squares in the figure), a 100 mM glycine-NaOH buffer solution (pH of 9.0 to 10.0, plotted with black ▲ triangles in the figure). The enzyme reaction was performed at 25° C. under different pH levels, so as to compare the relative activities. FIG. 5 shows the results. FIG. 5(A) and FIG. 5(B) respectively show the optimal activity pH examined using Geobacillus sp. Y4.1MC1-derived wild-type diaphorase and Geobacillus sp. Y4.1MC1-derived variant diaphorase of the present invention.

The results revealed that the optimal pH of wild-type diaphorase showed the highest activity value at the optimal activity pH of 7.3. Further, since the relative activity of 80% or more of the highest activity was observed at a pH range approximately from 6.7 to 8.0, it is believed that the wild-type diaphorase can be suitably used at this pH range.

The variant diaphorase exhibited the highest activity value at the optimal pH of 7.9. Further, since the relative activity of 60% or more of the highest activity was observed at a pH range approximately from 6.5 to 8.0, it is believed that the variant diaphorase can be suitably used at this pH range.

Example 12 pH Stability

The pH stability was measured using the diaphorase enzyme liquid (25 U/mL) obtained in Example 5. After being treated with a 100 mM potassium acetate buffer solution (pH of 5.0 to 6.0: plotted with black ♦ diamonds in the figure), a 100 mM potassium phosphate buffer solution (pH of 6.0 to 8.0, plotted with black ■ squares in the figure), and a 100 mM tris-HCl buffer solution (pH of 7.5 to 9.0, plotted with black ▲ triangles in the figure) for 16 hours at 25° C., the remaining activity of the enzyme liquid was measured. FIG. 6 shows the results. FIG. 6(A) and FIG. 6(B) respectively show the results of examining the pH stability of Geobacillus sp. Y4.1MC1-derived wild-type diaphorase and Geobacillus sp. Y4.1MC1-derived variant diaphorase of the present invention.

The results revealed that both the wild-type diaphorase and the variant diaphorase were stable at the pH range of 5.0 to 9.0.

Example 13

Temperature Stability

The temperature stability was measured using the diaphorase enzyme liquid (50 U/mL) obtained in Example 5. After treating the diaphorase enzyme liquid with a 100 mM potassium acetate buffer solution (pH of 7.5) at each temperature (50° C., 60° C., and 70° C.) for 15 to 60 minutes, the apparent remaining activity of the enzyme liquid was measured. FIG. 7 shows the results. FIG. 7(A) and FIG. 7(B) respectively show the temperature stability of Geobacillus sp. Y4.1MC1-derived wild-type diaphorase and Geobacillus sp. Y4.1MC1-derived variant diaphorase of the present invention. Furthermore, the temperature stability of Geobacillus stearothermophilus-derived diaphorase (produced by Unitika Ltd.) was examined in the same manner (FIG. 8).

The results revealed that the wild-type diaphorase exhibited 83% remaining activity after treatment at 70° C. for 60 minutes, and exhibited a higher remaining activity after treatment at 70° C. or lower (remaining activity of 90% or more at 50° C. and 60° C.). In contrast, Geobacillus stearothermophilus-derived diaphorase (produced by Unitika Ltd.) exhibited remaining activity of 44% after treatment at 70° C. for 60 minutes. This indicates that the wild-type diaphorase of the present invention is stable at a temperature of 70° C. or lower.

The wild-type diaphorase of the present invention exhibited remaining activity of 90% or more after treatment at 4° C., 30° C., and 40° C. for 60 minute, confirming its stability in a wide temperature range.

The wild-type diaphorase exhibited remaining activity of 90% or more after treatment at 50° C., 60° C., and 70° C. for 15 minutes.

The variant diaphorase of the present invention exhibited remaining activity of 88.5% after treatment at 70° C. for 60 minutes, and exhibited higher remaining activity after treatment at 70° C. or lower (remaining activity of 90% or more at 50° C. and 60° C.). This indicates that the variant diaphorase is stable at a temperature of 70° C. or lower.

Example 14

Measurement of Km Value with Respect to NADH

Figure 10:
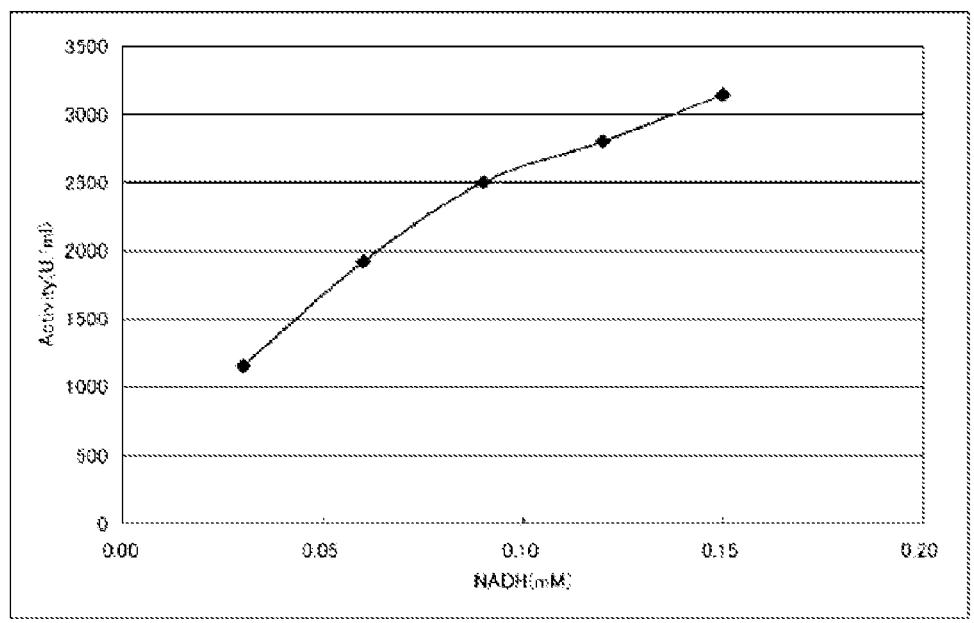
FIG. 10 shows the relationship between the reaction rate of the *Geobacillus stearothermophilus*-derived diaphorase (produced by Unitika Ltd.) and the NADH concentration.

The activity was measured by changing the concentration of NADH, which is the substrate, using the diaphorase activity measurement method described above, thereby obtaining a Lineweaver-Burk plot based on a graph in relation to the substrate concentration and reaction rate (FIGS. 9(A) and 9(B)) to determine the Km value. The Km value of the Geobacillus sp. Y4.1MC1-derived wild-type diaphorase for NADH was 0.073 mM (FIG. 9(A)). In the same manner, the activity of the Geobacillus sp. Y4.1MC1-derived variant diaphorase of the present invention was measured. The results revealed that the Km value of the variant diaphorase of the present invention for NADH was 0.363 mM (FIG. 9(B)). Furthermore, the activity of the Geobacillus stearothermophilus-derived diaphorase (produced by Unitika Ltd.) was measured in the same manner (FIG. 10). The results revealed that the Km value of the *Geobacillus stearothermophilus*-derived diaphorase (produced by Unitika Ltd.) for NADH was 0.115 mM.

Example 15

Specific Activity when ANQ is Used as a Mediator

Using the diaphorase enzyme liquid (0.01 to 0.02 mg/mL) obtained in Example 5, the reactivity to ANQ was measured (FIGS. 11(A) and (B)). The ANQ can be synthesized in the method as described in Non-patent Document 5, and can be used. The enzyme activities of *Geobacillus* sp. Y4.1MC1-derived wild-type diaphorase, *Geobacillus* sp. Y4.1MC1-derived variant diaphorase, and *Geobacillus stearothermophilus*-derived diaphorase (produced by Unitika Ltd.) were measured. The relation between the NADH concentration and the specific activity (U/mg) is shown in Table 1.

TABLE 1

| NADH Concentration (mM) | Wild type | G122D | Unitika Ltd. |
| --- | --- | --- | --- |
| 20 | 401.2 | 664.1 | 662.2 |
| 40 | 298.8 | 602.7 | 456.2 |
| 80 | 200.6 | 524.0 | 258.9 |

The results revealed that *Geobacillus* sp. Y4.1MC1-derived variant diaphorase exhibited a specific activity greater than *Geobacillus* sp. Y4.1MC1-derived wild-type diaphorase by a factor of 1.7 to 2.6 (FIG. 11(A)).

When the NADH concentration is 20 mM or more, it became clear that *Geobacillus* sp. Y4.1MC1-derived variant diaphorase had a higher specific activity than that of *Geobacillus stearothermophilus*-derived diaphorase (produced by Unitika Ltd.).

The diaphorase activity inhibition effect due to the high-concentration NADH is shown in FIG. 11(B). FIG. 11(B) is a graph showing the relative activity when the enzyme activity in 20 mM NADH is taken as 100%. The results indicate that *Geobacillus* sp. Y4.1MC1-derived variant diaphorase had a relative activity of 79% at 80 mM NADH. *Geobacillus* sp. Y4.1MC1-derived wild-type diaphorase had a relative activity of 50% at 80 mM NADH. *Geobacillus stearothermophilus*-derived diaphorase (produced by Unitika Ltd.) had a relative activity of 39% at 80 mM NADH.

The results indicate that the activity inhibition of the variant diaphorase of the present invention is suppressed compared to the wild-type when the NADH concentration is high.

Example 16

Temperature Dependence when DCPIP is Used as a Mediator

Using the diaphorase enzyme liquid obtained in Example 5, the temperature dependence was measured by the diaphorase activity measurement method described in Section 1-1-1 at 25° C., 30° C., and 37° C. The temperature dependence defined by 1-6 is shown in FIG. 12(A). The relationship between the reaction temperature and the specific activity is shown in FIG. 12(B).

As shown in FIG. 12(A), the relative value of *Geobacillus* sp. Y4.1MC1-derived variant diaphorase at 25° C. was 79.6% that at 37° C. However, the relative value of *Geobacillus* sp. Y4.1MC1-derived wild-type diaphorase at 25° C. was 61.3% that at 37° C. The relative value of *Geobacillus stearothermophilus*-derived diaphorase (produced by Unitika Ltd.) at 25° C. was 69.6% that at 37° C. The results indicate that the variant diaphorase of the present invention has an improved temperature dependence compared to the wild-type diaphorase.

The relative value of *Geobacillus* sp. Y4.1MC1-derived variant diaphorase at 25° C. was 93.0% that at 30° C. The relative value of *Geobacillus* sp. Y4.1MC1-derived wild-type diaphorase at 25° C. was 84.1% of that at 30° C. The relative value of *Geobacillus stearothermophilus*-derived diaphorase (produced by Unitika Ltd.) at 25° C. was 83.7% that at 30° C. The results revealed that the variant diaphorase of the present invention exhibited particularly improved temperature dependence in the temperature range of 25 to 30° C., which is close to room temperature, compared to the wild-type diaphorase.

Example 17

Temperature Dependence when ANQ is Used as Mediator

Using the diaphorase enzyme liquids obtained in Examples 4 and 5, the temperature dependence of the diaphorase in 20 mM NADH was measured at 25° C., 30° C., and 37° C., with the method for measuring diaphorase activity described in Section 1-1-2 above. FIG. 13(A) shows the temperature dependence defined in Section 1-6. FIG. 13(B) shows the relationship between the reaction temperature and specific activity.

As shown in FIG. 13(A), the remaining activity of *Geobacillus* sp. Y4.1MC1-derived variant diaphorase at 25° C. was 52.9% relative to that at 37° C. The remaining activity of *Geobacillus* sp. Y4.1MC1-derived wild-type diaphorase at 25° C. was 36.0% relative to that at 37° C. The remaining activity of *Geobacillus stearothermophilus*-derived diaphorase (produced by Unitika Ltd.) at 25° C. was 46.3% relative to that at 37° C. The results revealed that the variant diaphorase of the present invention had improved temperature dependence compared to wild-type diaphorase.

*Geobacillus* sp. Y4.1MC1-derived variant diaphorase exhibited the remaining activity at 25° C. of 98.0% relative to that at 30° C. In contrast, *Geobacillus* sp. Y4.1MC1-derived wild-type diaphorase exhibited the relative value at 25° C. of 59.0% that at 30° C. *Geobacillus stearothermophilus*-derived diaphorase (produced by Unitika Ltd.) exhibited the relative value at 25° C. of 83.0% that at 30° C. The results revealed that the variant diaphorase of the present invention exhibited particularly improved temperature dependence in the temperature range of 25 to 30° C., which is close to room temperature, compared to the wild-type diaphorase.

The results indicate that the variant diaphorase of the present invention has improved temperature dependence compared to a wild-type diaphorase. In particular, the temperature dependence near room temperature (25 to 30° C.) is clearly improved.

As shown in FIG. 13(B), *Geobacillus* sp. Y4.1MC1-derived variant diaphorase exhibited specific activity higher than that of *Geobacillus* sp. Y4.1MC1-derived wild-type diaphorase and *Geobacillus stearothermophilus*-derived diaphorase (produced by Unitika Ltd.) at any temperature in the range of 25 to 37° C. The specific activity of *Geobacillus* sp. Y4.1MC1-derived wild-type diaphorase at 37° C. was 678.8 U/mg. In contrast, the specific activity of *Geobacillus* sp. Y4.1MC1-derived variant diaphorase was 942.8 U/mg, which is greater by a factor of 1.39 times. The specific activity of *Geobacillus* sp. Y4.1MC1-derived wild-type diaphorase at 30° C. was 413.3 U/mg, and that of *Geobacillus* sp. Y4.1MC1-derived variant diaphorase was 509.6 U/mg (1.23 times). In particular, the specific activity at 25° C. of *Geobacillus* sp. Y4.1MC1-derived wild-type diaphorase was 244.2 U/mg, and that of *Geobacillus* sp. Y4.1MC1-derived variant diaphorase was 498.8 U/mg, which is 2 times or more that of wild-type diaphorase.

These results revealed that the temperature dependence of the variant diaphorase of the present invention, when a naphthoquinone derivative is used as a mediator, is improved compared to wild-type diaphorase. Furthermore, the specific activity thereof is improved compared to wild-type diaphorase. This effect is remarkable, in particular, in the range of 25 to 37° C.

This invention is not limited to the above Embodiments and Examples. The invention also includes variations and modifications within the scope of the patent claims set forth below and within a range readily conceived by those skilled in the art.

The entire contents of papers, laid-open patent applications, and patent publications referred to in this specification are incorporated herein by reference.

INDUSTRIAL APPLICABILITY

The diaphorase of the invention has excellent affinity for NADH, and is capable of accurately measuring the amount of NADH. The diaphorase of the invention is thus suitable, for example, for measuring NADH.

The invention claimed is:

1. A diaphorase comprising any one of the following polypeptides (a) to (b):
   (a) a polypeptide having the amino acid sequence of SEQ ID NO: 1 in which up to about 20% of the amino acid residues of SEQ ID NO: 1 are substituted, deleted, inserted, added, and/or inverted, and having diaphorase activity, and
   (b) a polypeptide having an amino acid sequence with 80% or more identity to the amino acid sequence of SEQ ID NO: 1, and having diaphorase activity,
   wherein said polypeptide is not the amino acid sequence of SEQ ID NO: 1.

2. The diaphorase according to claim 1, wherein the diaphorase has the following properties (1) to (5):
   (1) Subunit molecular weight: the molecular weight of a polypeptide moiety in the enzyme is about 23.7 kDa as measured by SDS-polyacrylamide electrophoresis,
   (2) Composite molecular weight: the molecular weight of a polypeptide moiety in the enzyme is about 53.3 kDa as measured by gel filtration,
   (3) Km value: the Km value for NADH is about 0.1 mM or less,
   (4) Temperature stability: stable at a temperature of 70° C. or lower,
   (5) pH stability: stable at a pH range of 5.0 to 9.0,
   wherein position 122 of the polypeptide is aspartic acid.

3. The diaphorase according to claim 1, which is a variant diaphorase having any one of the following polypeptides (a) to (c):
   (a) a polypeptide having the amino acid sequence of SEQ ID NO: 4,
   (b) a polypeptide having the amino acid sequence of SEQ ID NO: 4 in which up to about 20% of the amino acid residues are substituted, deleted, inserted, added, and/or inverted at a position other than position 122, wherein position 122, which is glycine in SEQ ID NO: 1, is aspartic acid, and having diaphorase activity, and
   (c) a polypeptide having an amino acid sequence with 80% or more identity to the amino acid sequence of SEQ ID NO: 4, wherein position 122, which is glycine in SEQ ID NO: 1, is aspartic acid and wherein the polypeptide has diaphorase activity.

4. The variant diaphorase according to claim 3, which further has one or more of the following properties (d) and (e):
   (d) when the specific activity in the presence of 20 mM NADH is taken as 100%, the specific activity in the presence of 80 mM NADH is maintained at 50% or more,
   (e) (1) when reacted with 2,6-dichloroindophenol and the activity value at 37° C. is taken as 100%, the relative activity at 25° C. is 70% or more, or (2) when reacted with a naphthoquinone derivative and the activity value at 37° C. is taken as 100%, the relative activity at 25° C. is 50% or more.

5. The variant diaphorase according to claim 3, which further has the following property (f):
   (f) when reacted with a naphthoquinone derivative, the specific activity is at least 1.5 times that of a wild-type diaphorase.

6. A product comprising the diaphorase of claim 1.

7. The diaphorase according to claim 2, which is a variant diaphorase having any one of the following polypeptides (a) to (c):
   (a) a polypeptide having the amino acid sequence of SEQ ID NO: 4,
   (b) a polypeptide having the amino acid sequence of SEQ ID NO: 4 in which up to about 20% of the amino acid residues are substituted, deleted, inserted, added, and/or inverted at a position other than position 122, wherein position 122 is aspartic acid, and having diaphorase activity, and
   (c) a polypeptide having an amino acid sequence with 80% or more identity to the amino acid sequence of SEQ ID NO: 4, wherein position 122, which is glycine in SEQ ID NO: 1, is aspartic acid and wherein the polypeptide has diaphorase activity,
   wherein said polypeptide is not the amino acid sequence of SEQ ID NO: 1.

8. The variant diaphorase according to claim 4, which further has the following property (f):
   (f) when reacted with a naphthoquinone derivative, the specific activity is at least 1.5 times that of a wild-type diaphorase.

9. The diaphorase according to claim 1, wherein the diaphorase has the amino acid sequence of SEQ ID NO: 1 in which up to about 15% of the amino acid residues of SEQ ID NO: 1 are substituted, deleted, inserted, added, and/or inverted, and has diaphorase activity.

10. The diaphorase according to claim 1, wherein the diaphorase has the amino acid sequence of SEQ ID NO: 1 in which up to about 10% of the amino acid residues of SEQ ID NO: 1 are substituted, deleted, inserted, added, and/or inverted, and has diaphorase activity.

11. The diaphorase according to claim 1, wherein the diaphorase has the amino acid sequence of SEQ ID NO: 1 in which up to about 5% of the amino acid residues of SEQ ID NO: 1 are substituted, deleted, inserted, added, and/or inverted, and has diaphorase activity.

12. The diaphorase according to claim 1, wherein the diaphorase has the amino acid sequence of SEQ ID NO: 1 in which less than 1% of the amino acid residues of SEQ ID NO: 1 are substituted, deleted, inserted, added, and/or inverted, and has diaphorase activity.

13. The diaphorase according to claim 1, wherein the diaphorase is freeze-dried.

14. A kit comprising:
   the diaphorase according to claim 1,
   wherein the diaphorase is freeze-dried.

15. A sensor comprising:
   the diaphorase according to claim 1,
   wherein the diaphorase is freeze-dried.

16. A sensor comprising:
   an electrode, and
   the diaphorase according to claim 1,
   wherein the diaphorase is immobilized on the electrode.

* * * * *

SEQUENCE LISTING

```
<160> NUMBER OF SEQ ID NOS: 5

<210> SEQ ID NO 1
<211> LENGTH: 211
<212> TYPE: PRT
<213> ORGANISM: Geobacillus sp. Y4.1MC1

<400> SEQUENCE: 1

Met Ala Lys Leu Leu Tyr Ile Thr Ala Asn Pro Lys Arg Glu Glu
1               5                   10                  15

Ser Tyr Ser Leu Ser Val Gly Arg Ala Phe Leu Asn Ala Tyr Lys Gln
                20                  25                  30

Gln Asn Pro Gln Asp Glu Ile Ile Glu Leu Asp Leu Tyr Arg Thr Asp
            35                  40                  45

Ile Pro Tyr Ile Asp Ala Asp Val Leu Asn Gly Trp Gly Lys Leu Gln
        50                  55                  60

Gln Gly Gln Ser Phe Asp Gln Leu Ser Ala Glu Lys Gln Lys Ile
65                  70                  75                  80

Ser Arg Ile Asn Glu Leu Thr Asp Gln Phe Ile Ser Ala Asp Lys Tyr
                85                  90                  95

Val Phe Val Thr Pro Met Trp Asn Phe Ser Phe Pro Pro Lys Met Lys
                100                 105                 110

Ala Tyr Ile Asp Thr Ile Cys Ile Ala Gly Lys Thr Phe Arg Tyr Thr
            115                 120                 125

Glu Asn Gly Ser Val Gly Leu Leu Thr Gly Arg Lys Ala Val His Ile
        130                 135                 140

Gln Ala Arg Gly Gly Ile Tyr Ser Glu Gly Pro Thr Lys Glu Val Glu
145                 150                 155                 160

Phe Gly Asp Arg Tyr Leu Arg Ala Val Leu Gly Phe Ile Gly Ile Thr
                165                 170                 175

Asp Val Gln Ser Val Ile Val Glu Gly Met Ala Gln Phe Pro Asn Glu
                180                 185                 190

Ala Glu Ser Ile Lys Glu Asn Ala Ile Lys Arg Ala Glu Gln Val Ala
            195                 200                 205

Lys Asn Phe
    210

<210> SEQ ID NO 2
<211> LENGTH: 636
<212> TYPE: DNA
<213> ORGANISM: Geobacillus sp. Y4.1MC1
```

<400> SEQUENCE: 2

```
atggccaaac tattgtacat tacggcaaat ccaaaacggg aagaagaatc ttacagctta    60
tccgtcggca gagcgtttct gaacgcttat aaacagcaaa acccgcaaga tgaaattatc   120
gaattagacc tttaccgcac cgatatccct tatatcgatg ccgacgtgtt gaacggctgg   180
ggcaaattac agcaaggaca atcatttgac caattaagtg cagaggaaaa acaaaaaata   240
agccgcatta cgaactaac cgatcaattc atcagcgcgg ataaatatgt gtttgtcaca   300
ccaatgtgga actttagttt tccaccgaaa atgaaagcat atattgatac aatttgcatc   360
gcaggaaaaa cgttccgtta cactgaaaat ggttcagtag gctattaac aggaagaaaa   420
gcagtgcaca ttcaagcgcg cggcggaatt tattcagaag ggccaacgaa agaagtagaa   480
tttggcgacc gttatttacg ggcagtgctt ggctttatcg gcattactga cgttcaatcc   540
gttatcgttg aaggaatggc gcaattcccg aatgaagccg aatccattaa ggaaaacgcg   600
atcaagcgcg cagaacaagt agcgaaaaac ttttaa                              636
```

<210> SEQ ID NO 3
<211> LENGTH: 211
<212> TYPE: PRT
<213> ORGANISM: Geobacillus stearothermophilus (ACCESSION AAD24436)

<400> SEQUENCE: 3

```
Met Thr Asn Val Leu Tyr Ile Thr Ala His Pro His Asp Asp Thr Gln
1               5                  10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210
```

<210> SEQ ID NO 4
<211> LENGTH: 211
<212> TYPE: PRT
<213> ORGANISM: Geobacillus sp. Y4.1MC1 mutant

<400> SEQUENCE: 4

```
Met Ala Lys Leu Leu Tyr Ile Thr Ala Asn Pro Lys Arg Glu Glu
1               5                   10                  15

Ser Tyr Ser Leu Ser Val Gly Arg Ala Phe Leu Asn Ala Tyr Lys Gln
            20                  25                  30

Gln Asn Pro Gln Asp Glu Ile Ile Glu Leu Asp Leu Tyr Arg Thr Asp
        35                  40                  45

Ile Pro Tyr Ile Asp Ala Asp Val Leu Asn Gly Trp Gly Lys Leu Gln
    50                  55                  60

Gln Gly Gln Ser Phe Asp Gln Leu Ser Ala Glu Lys Gln Lys Ile
65                  70                  75                  80

Ser Arg Ile Asn Glu Leu Thr Asp Gln Phe Ile Ser Ala Asp Lys Tyr
                85                  90                  95

Val Phe Val Thr Pro Met Trp Asn Phe Ser Phe Pro Pro Lys Met Lys
            100                 105                 110

Ala Tyr Ile Asp Thr Ile Cys Ile Ala Asp Lys Thr Phe Arg Tyr Thr
        115                 120                 125

Glu Asn Gly Ser Val Gly Leu Leu Thr Gly Arg Lys Ala Val His Ile
    130                 135                 140

Gln Ala Arg Gly Gly Ile Tyr Ser Glu Gly Pro Thr Lys Glu Val Glu
145                 150                 155                 160

Phe Gly Asp Arg Tyr Leu Arg Ala Val Leu Gly Phe Ile Gly Ile Thr
                165                 170                 175

Asp Val Gln Ser Val Ile Val Glu Gly Met Ala Gln Phe Pro Asn Glu
            180                 185                 190

Ala Glu Ser Ile Lys Glu Asn Ala Ile Lys Arg Ala Glu Gln Val Ala
        195                 200                 205

Lys Asn Phe
    210
```

<210> SEQ ID NO 5
<211> LENGTH: 636
<212> TYPE: DNA
<213> ORGANISM: Geobacillus sp. Y4.1MC1 mutant

<400> SEQUENCE: 5

```
atggccaaac tattgtacat tacggcaaat ccaaaacggg aagaagaatc ttacagctta      60
tccgtcggca gagcgtttct gaacgcttat aaacagcaaa acccgcaaga tgaaattatc     120
gaattagacc tttaccgcac cgatatccct tatatcgatg ccgacgtgtt gaacggctgg     180
ggcaaattac agcaaggaca atcatttgac caattaagtg cagaggaaaa acaaaaaata     240
agccgcatta cgaactaac cgatcaattc atcagcgcgg ataaatatgt gtttgtcaca     300
ccaatgtgga actttagttt tccaccgaaa atgaaagcat atattgatac aatttgcatc     360
gcagataaaa cgttccgtta cactgaaaat ggttcagtag gctattaac aggaagaaaa     420
gcagtgcaca ttcaagcgcg cggcggaatt tattcagaag ggccaacgaa agaagtagaa     480
tttggcgacc gttatttacg ggcagtgctt ggctttatcg gcattactga cgttcaatcc     540
gttatcgttg aaggaatggc gcaattcccg aatgaagccg aatccattaa ggaaaacgcg     600
atcaagcgcg cagaacaagt agcgaaaaac ttttaa                              636
```